(12) United States Patent
Shishino et al.

(10) Patent No.: US 11,401,400 B2
(45) Date of Patent: Aug. 2, 2022

(54) PLASTIC LENS

(71) Applicants: Tokai Optical Co., Ltd., Okazaki (JP); Miyoshi Oil & Fat Co., Ltd., Tokyo (JP)

(72) Inventors: Yuichi Shishino, Aichi (JP); Shingo Ono, Aichi (JP); Koji Kawai, Tokyo (JP); Kotaro Kaneko, Tokyo (JP); Nobuhiro Kaneko, Tokyo (JP)

(73) Assignees: TOKAI OPTICAL CO., LTD., Aichi (JP); MIYOSHI OIL & FAT CO., LTD., Tokyo (JP)

( * ) Notice: Subject to any disclaimer, the term of this patent is extended or adjusted under 35 U.S.C. 154(b) by 0 days.

(21) Appl. No.: 15/569,803

(22) PCT Filed: Oct. 21, 2015

(86) PCT No.: PCT/JP2015/079745
§ 371 (c)(1),
(2) Date: Oct. 27, 2017

(87) PCT Pub. No.: WO2016/174788
PCT Pub. Date: Nov. 3, 2016

(65) Prior Publication Data
US 2018/0134872 A1 May 17, 2018

(30) Foreign Application Priority Data
Apr. 30, 2015 (JP) .............................. JP2015-093685

(51) Int. Cl.
*C08K 5/378* (2006.01)
*G02B 5/22* (2006.01)
(Continued)

(52) U.S. Cl.
CPC ............ *C08K 5/378* (2013.01); *C07D 249/20* (2013.01); *C08K 5/36* (2013.01); *G02B 1/04* (2013.01);
(Continued)

(58) Field of Classification Search
CPC ........ C08K 5/378; C08K 5/36; C07D 249/20; G02B 1/04; G02B 1/041; G02B 5/22; G02C 7/10
(Continued)

(56) References Cited
U.S. PATENT DOCUMENTS

| | | | |
|---|---|---|---|
| 5,298,380 A | 3/1994 | Leppard | |
| 2001/0007886 A1 | 7/2001 | Ravichandran et al. | |

(Continued)

FOREIGN PATENT DOCUMENTS

| | | |
|---|---|---|
| CN | 106687550 | 5/2017 |
| EP | 0599269 | * 11/1993 |

(Continued)

OTHER PUBLICATIONS

International Search Report dated Jan. 12, 2016 in International (PCT) Application No. PCT/JP2015/079745.
Office Action dated Oct. 9, 2019 in corresponding Chinese Patent Application No. 201580079380.5, with English translation.

*Primary Examiner* — Ling Siu Choi
*Assistant Examiner* — Ronald Grinsted
(74) *Attorney, Agent, or Firm* — Wenderoth, Lind & Ponack, L.L.P.

(57) ABSTRACT

To provide a plastic lens which can absorb light with a wavelength of 400 to 420 nm with sufficiently high efficiency but is reduced in the absorption of light with a wavelength of around 420 nm or longer, is less affected by harmful light, suppresses yellow coloration and therefore has excellent appearance, suppresses yellowish discoloration over time, and has excellent heat resistance, light resistance, and also optical performance, particularly an excellent Abbe's number.
The plastic lens is characterized by containing an ultraviolet absorbing agent represented by the following formula (I):

[Chemical Formula 1]

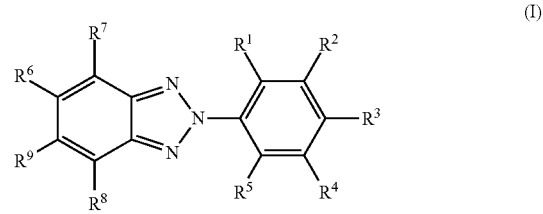

(in the formula, $R^1$ to $R^8$ each independently represent a monovalent group such as a hydrogen atom, $R^9$ represents a monovalent sulfur-containing group represented by the following formula (i):

[Chemical Formula 2]

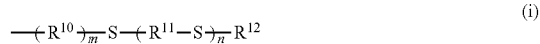

(in the formula, $R^{10}$ represents a divalent hydrocarbon group with 1 to 20 carbon atoms or the like; $R^{11}$ represents a divalent hydrocarbon group with 1 to 20 carbon atoms or the like; $R^{12}$ represents a monovalent hydrocarbon group with 1 to 20 carbon atoms; the total number of carbon atoms in $R^{10}$, n number of $R^{11}$, and $R^{12}$ is 30 or less; m represents an integer of 0 or 1; and n represents an integer of 0 to 3)), and a resin material.

19 Claims, 10 Drawing Sheets

(51) Int. Cl.
  *G02C 7/10* (2006.01)
  *G02B 1/04* (2006.01)
  *C08K 5/36* (2006.01)
  *C07D 249/20* (2006.01)
(52) U.S. Cl.
  CPC ............... *G02B 1/041* (2013.01); *G02B 5/22* (2013.01); *G02C 7/10* (2013.01)
(58) Field of Classification Search
  USPC ........................................................ 252/589
  See application file for complete search history.

(56) References Cited

U.S. PATENT DOCUMENTS

| | | |
|---|---|---|
| 2002/0171606 A1 | 11/2002 | Yabuki |
| 2007/0092831 A1 | 4/2007 | Lai et al. |
| 2017/0217937 A1 | 8/2017 | Kawai et al. |

FOREIGN PATENT DOCUMENTS

| | | | |
|---|---|---|---|
| EP | 0698637 | * | 8/1995 |
| EP | 0 698 637 | | 2/1996 |
| JP | 2005-292240 | | 10/2005 |
| JP | 2006-235587 | | 9/2006 |
| JP | 4334633 | | 9/2009 |
| JP | 2011-121214 | | 6/2011 |
| JP | 5620033 | | 11/2014 |
| WO | 92/14717 | | 9/1992 |
| WO | 92/14718 | | 9/1992 |

\* cited by examiner

Fig.22

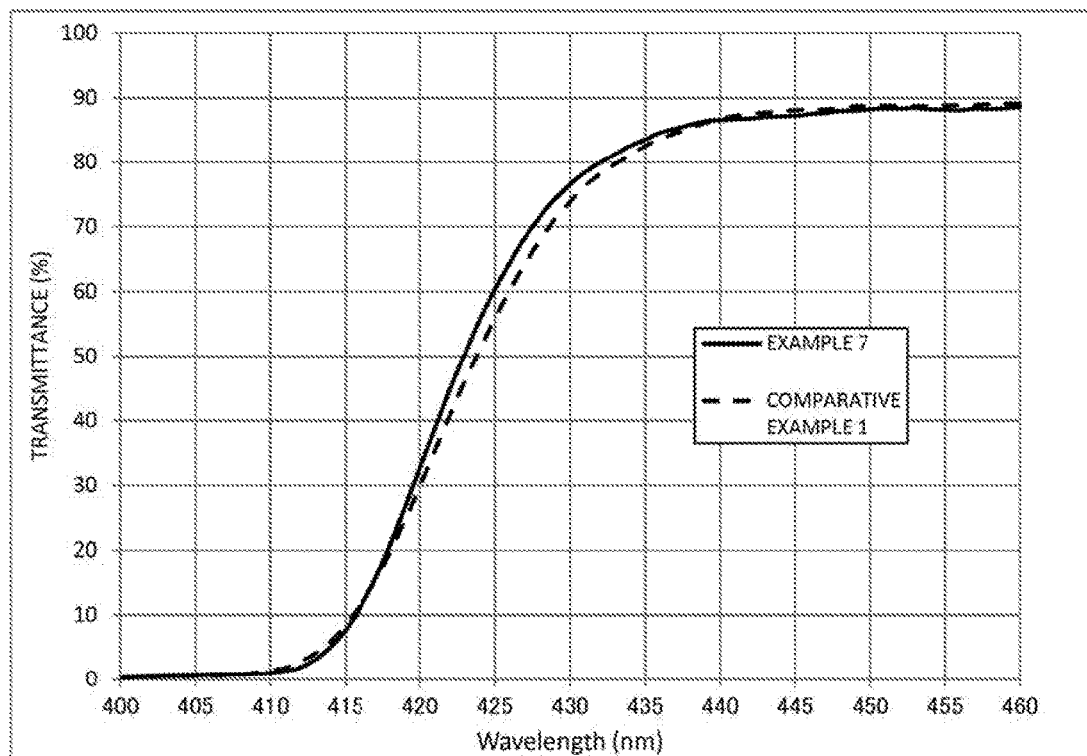

Fig.23

| CONCENTRATION | ABSORBANCE OF ABSORPTION PEAK IN WAVELENGTH RANGE OF FROM 350 TO 390 nm | ABSORBANCE OF PEAK END | ABSORPTION WAVELENGTH OF PEAK END | WAVELENGTH OF ABSORPTION PEAK IN WAVELENGTH RANGE OF FROM 350 TO 390 nm (MAXIMUM ABSORPTION WAVELENGTH: $\lambda_{max}$) | ABSOLUTE VALUE OF GRADIENT AT LONGER WAVELENGTH SIDE OF ABSORPTION PEAK IN WAVELENGTH RANGE OF FROM 350 TO 390 nm |
|---|---|---|---|---|---|
| 10μM | 0.21585 | 0.00013 | 427.5 | 367.0 | 0.00357 |
| 25μM | 0.7874 | 0.00343 | 427.0 | 367.0 | 0.01307 |
| 50μM | 1.69356 | 0.00541 | 427.0 | 367.0 | 0.02814 |

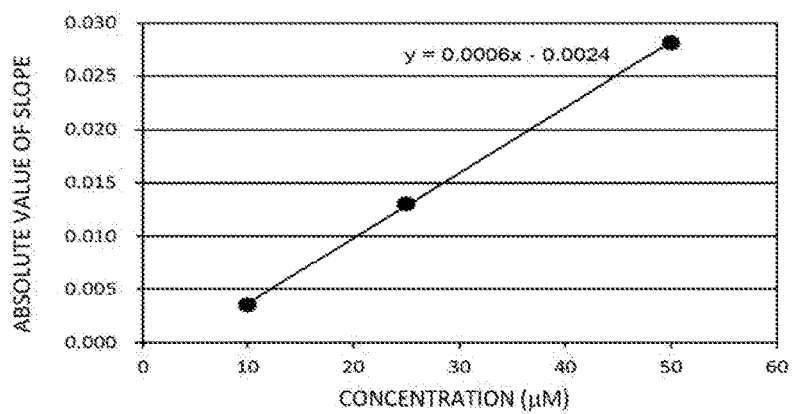

PLASTIC LENS

TECHNICAL FIELD

The present invention relates to an ultraviolet ray-absorbing plastic lens for protecting eyes from ultraviolet ray,

BACKGROUND ART

Compared to a glass lens, a plastic lens is lighter weight, less fragile, more prone to coloring, and easier for fine molding. As such, in recent years, it is rapidly applied for an optical lens product such as an eyeglass lens, a contact lens, or a camera lens.

Because the properties of a plastic lens are deteriorated by thermal history or exposure to ultraviolet ray, for example over a long period of time, yellowish discoloration of the lens is unavoidable, and thus it is required for the plastic lens to have an improvement in terms of heat yellowing resistance and light yellowing resistance so as not to have any inhibition on a use for a long period of time.

In recent years, not only for the purpose of improving the light resistance of a resin itself against ultraviolet ray like sunlight but also for protecting eyes, determinations are also made for providing a plastic lens with an ultraviolet ray absorbing property. The harmful effect of exposure of eyes to ultraviolet ray has been noted before, and there is concern regarding an influence of blue light that is included in natural light or light emitted from a liquid crystal display of an office instrument, and a display of a portable device such as smart phone or cellular phone, i.e., tired feeling or pain in eyes. For example, it is recognized that irradiation of an eye with blue light for long period of time leads to Asthenopia eye strain or exposure to oxidative stress caused by an occurrence of reactive oxygen species, in particular, excessive singlet oxygen. It is found that generation of the singlet oxygen is promoted by blue light with short wavelength, which has higher energy among ultraviolet ray and visible light. It is also believed that, in retina, as a waste called lipofuscin is accumulated in retinal pigment epithelium according to aging, it functions as a photosensitizing material to generate singlet oxygen. Lipofuscin has a property of having higher absorption as wavelength range from visible to ultraviolet shorter. Incidentally, lutein is known to suppress oxidative stress caused by singlet oxygen. Although lutein is present in a retina, it is deteriorated by ultraviolet to blue light.

For such reasons, for inhibiting an occurrence of singlet oxygen by lipofuscin and inhibiting a deterioration of lutein which suppresses an oxidative stress, it is very effective to cut, before retina, the wavelength of 400 to 420 nm which corresponds to a wavelength range in which the light absorption property is overlapped between lutein and lipofuscin. Furthermore, according to the recent study, once a retinal tissue is exposed to light with a short wavelength of 411 nm, the neural retinal cells experience higher oxidative stress than a case of exposure to light with a wavelength of 470 nm, and thus symptoms of cell death are observed or an occurrence of a structural change of the retinal tissue is shown, and they are considered to be one of the reasons for having a progress of age-related macular degeneration, for example. Furthermore, since it has been shown that generation of reactive oxygen species as a cause of cortical cataract, damage of DNA, and cell death of lens epithelial cells are initiated by irradiation of light with a wavelength of 400 to 420 nm, blocking the light with a short wavelength of 400 to 420 nm, which has a possibility to become a trigger of a disorder in eye tissues, is very important to maintain eyes in healthy state.

Furthermore, in visible light, the light with a wavelength of 400 to 420 nm has a wavelength with lower sensitivity, and it exhibits little influence on lowered visual function in a dark place or circadian rhythm.

Accordingly, use of an ultraviolet absorbing agent for absorbing light with a wavelength of 400 to 420 nm in a plastic lens is proposed (Patent Literatures 1 and 2), In Patent Literature 1, a technique of using 2-(2-hydroxy-3-t-butyl-5-methylphenyl)-chlorobenzotriazole as an ultraviolet absorbing agent and combining it with a resin material like episulfide resin is proposed.

CITATION LIST

Patent Literature

Patent Literature 1: JP 5620033 B
Patent Literature 2: JP 4334633 B

SUMMARY OF INVENTION

Technical Problem

However, when it is tried to have sufficient absorption of light with a wavelength near 400 to 420 nm by adding 2-(2-hydroxy-3-t-butyl-5-methylphenyl)-chloroberizotriazole as an ultraviolet absorbing agent to a resin, the absorption efficiency in that wavelength region is low so that a large addition amount is required and, at the same time, the light with longer wavelength than 420 nm is also absorbed a lot due to its optical characteristics, and thus there is a problem of having yellow coloration of a lens.

The present invention is achieved under the circumstances described above, and object of the present invention is to provide a plastic lens which can absorb light with a wavelength of 400 to 420 nm with sufficiently high efficiency but is reduced in the absorption of light with a wavelength of around 420 nm or longer, is less affected by harmful light, suppresses yellow coloration and therefore has excellent appearance, suppresses yellowish discoloration of a lens over time, and has excellent heat resistance, light resistance, and also optical performance, particularly an excellent Abbe's number.

Solution to Problem

To solve the problems described above, the plastic lens of the present invention contains an ultraviolet absorbing agent which is represented by the following formula (I):

[Chemical Formula 1]

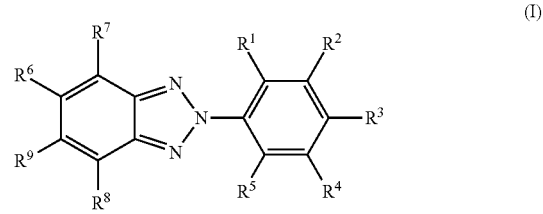

(I)

(in the formula, $R^1$ to $R^8$ each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom. $R^9$ represents a monovalent sulfur-containing group which is represented by the following formula (i):

[Chemical Formula 2]

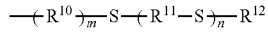 (i)

(in the formula, $R^{10}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom, represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom when n is 2 or higher, $R^{12}$ represents a hydrogen atom or a group represented by $—(R^{13})_p—R^{14}$ ($R^{13}$ represents a divalent hydrocarbon group with 1 to 20 carbon atoms which may be substituted a hydrogen atom with interrupted a proximal terminal by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom, and $R^{14}$ represents a hydrogen atom or a substituent group containing any one skeleton selected from benzotriazole, benzophenone, benzoic acid ester, and triazine, p represents an integer of 0 or 1). Total number of carbon atoms in $R^{10}$, n number of $R^{11}$, and $R^{12}$ is 30 or less. m represents an integer of 0 or 1. n represents an integer of 0 to 3)); and a resin material.

Advantageous Effects of Invention

According to the present invention, transmittance with a wavelength of around 420 nm or longer is favorable while the absorption effect higher than a related art is obtained in terms of transmittance for light with a short wavelength of less than 420 nm when compared to a case of using an ultraviolet absorbing agent of a related art. Thus, yellow coloration of a plastic lens as caused by an influence of an ultraviolet absorbing agent can be suppressed. Furthermore, as the ultraviolet absorbing effect (i.e., molar absorption coefficient) is high, harmful light with a wavelength of 400 to 420 nm can be sufficiently absorbed with small addition amount so that a negative influence on eyes can be suppressed. Furthermore, as the ultraviolet absorbing agent represented by the formula (I) has high compatibility with a monomer as a raw resin material of a plastic lens and a resin, exudation can be suppressed even after processing into a plastic lens. Furthermore, the heat resistance and light resistance for suppressing yellowish discoloration of a lens over time are excellent, and high optical performance of a plastic lens, particularly a high Abbe's number, can be obtained.

BRIEF DESCRIPTION OF DRAWINGS

FIG. 22 is a transmission spectrum of a plastic lens of Example 7 and Comparative Example 1.
FIG. 23 is a graph showing the absolute value of gradient at longer wavelength side of the absorption peak of the compound 5 and concentration of an ultraviolet absorbing agent.

DESCRIPTION OF EMBODIMENTS

Figure 1:
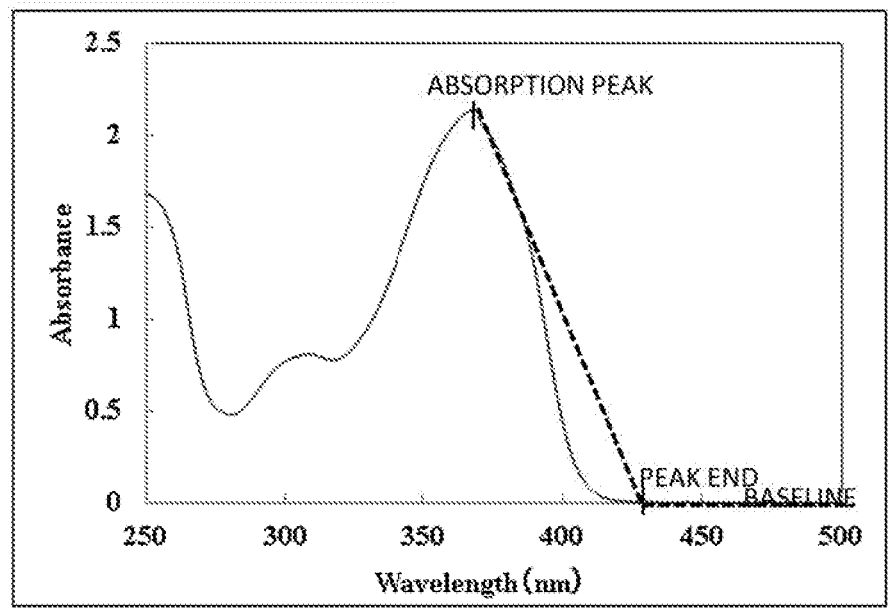
FIG. 1 is an absorption spectrum of the compound 1 (chloroform solution).
Figure 2:
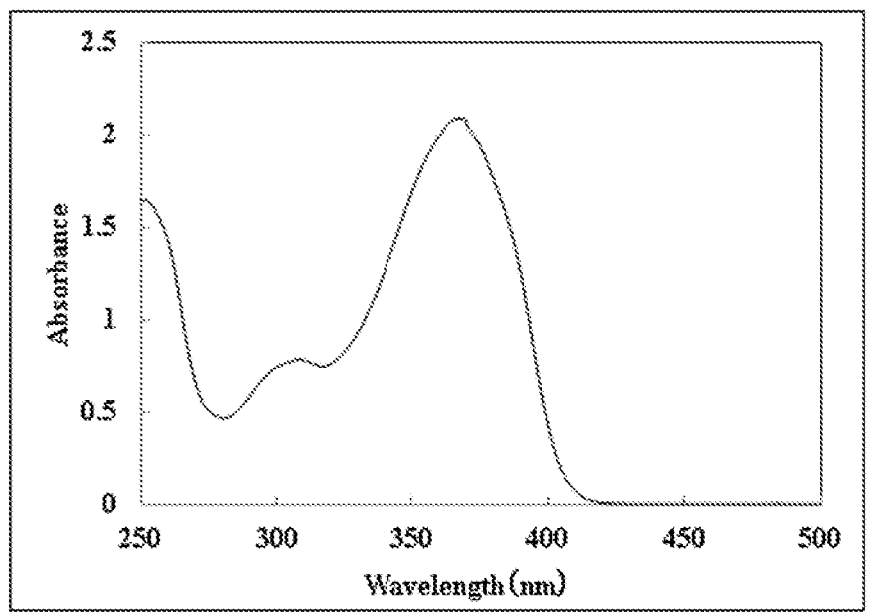
FIG. 2 is an absorption spectrum of the compound 2 (chloroform solution).
Figure 3:
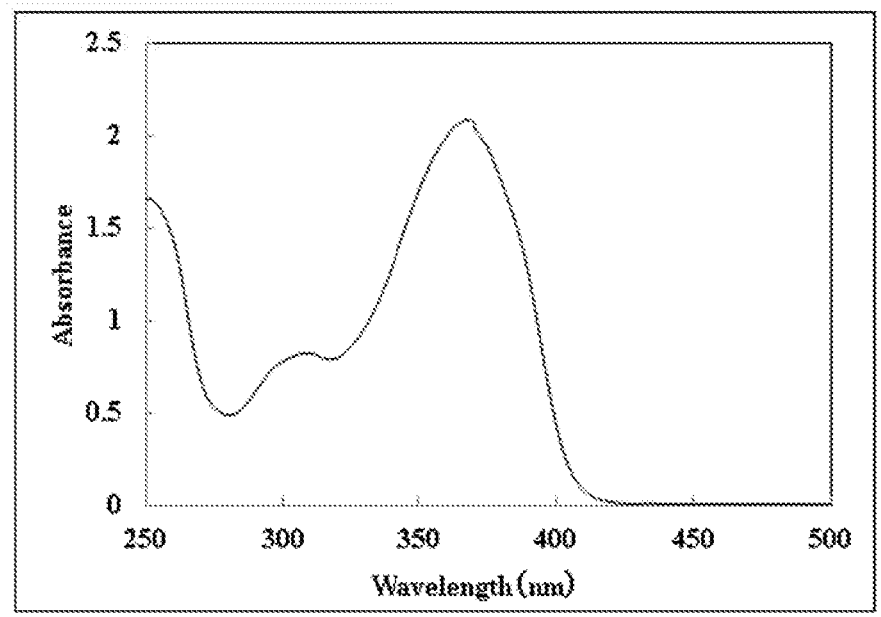
FIG. 3 is an absorption spectrum of the compound 3 (chloroform solution).
Figure 4:
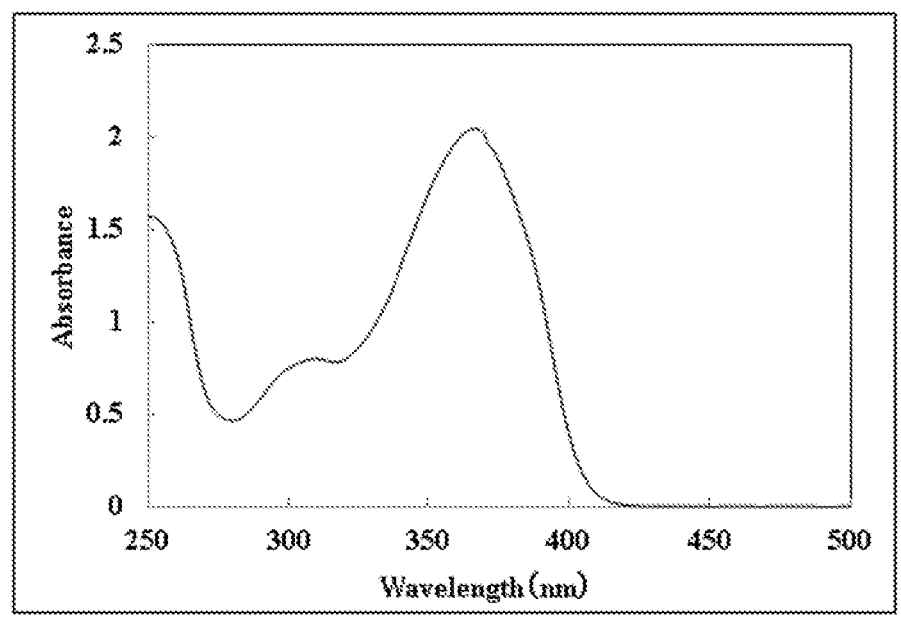
FIG. 4 is an absorption spectrum of the compound 4 (chloroform solution).
Figure 5:
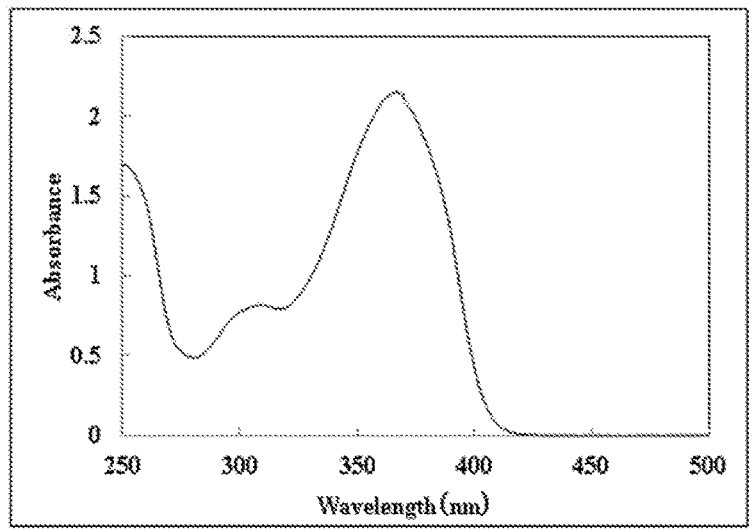
FIG. 5 is an absorption spectrum of the compound 5 (chloroform solution).
Figure 6:
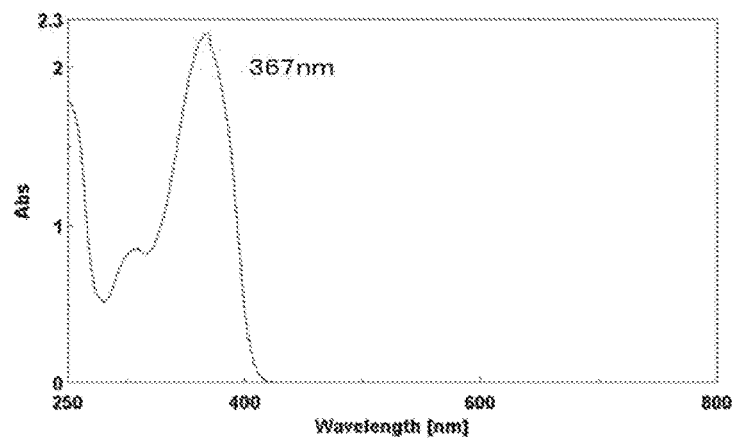
FIG. 6 is an absorption spectrum of the compound 6 (chloroform solution).
Figure 7:
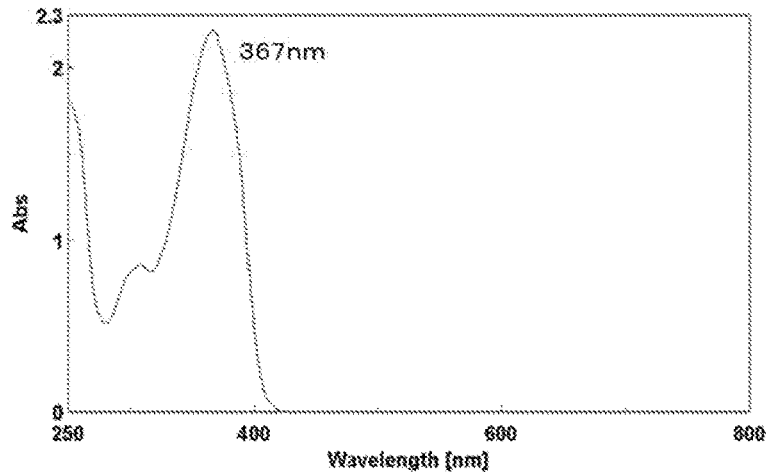
FIG. 7 is an absorption spectrum of the compound 7 (chloroform solution).
Figure 8:
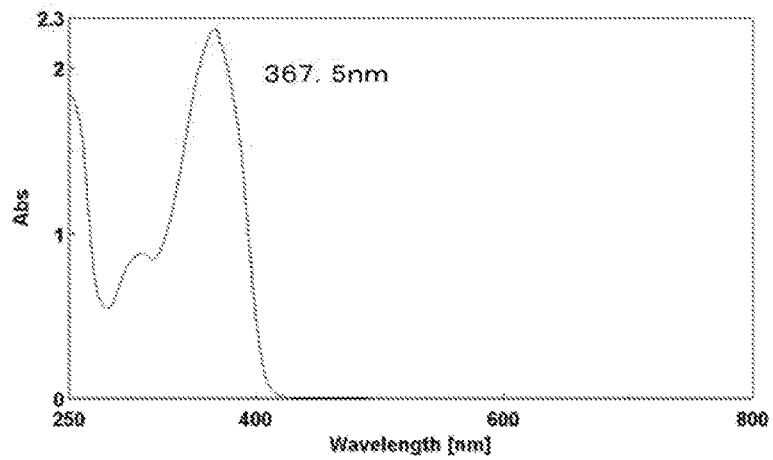
FIG. 8 is an absorption spectrum of the compound 8 (chloroform solution).
Figure 9:
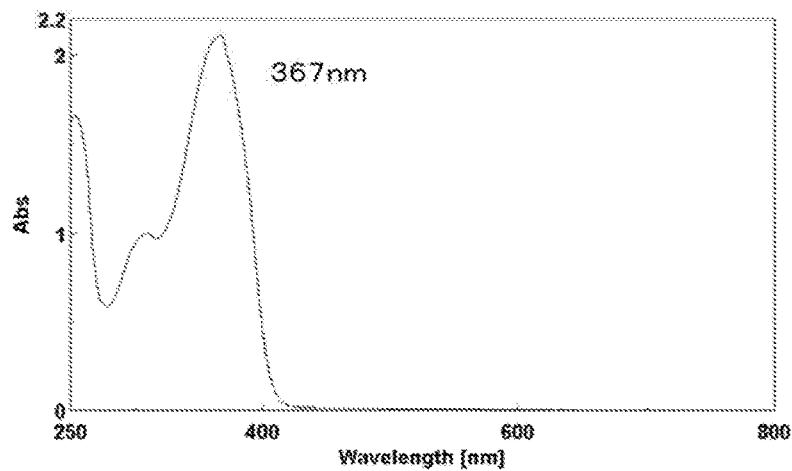
FIG. 9 is an absorption spectrum of the compound 9 (chloroform solution).
Figure 10:
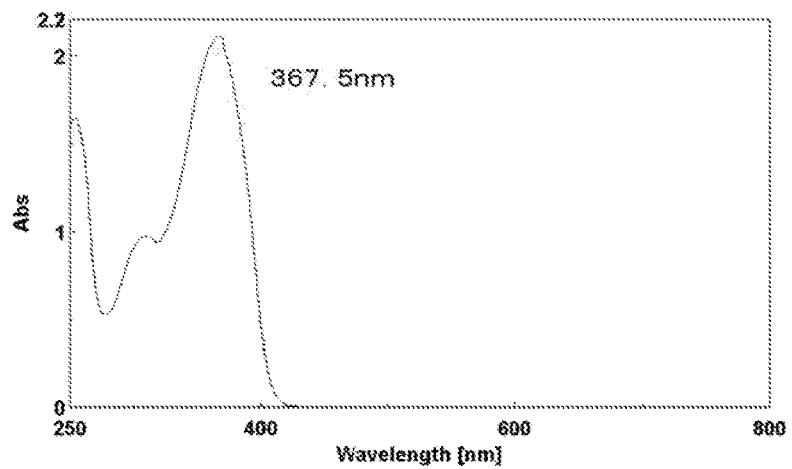
FIG. 10 is an absorption spectrum of the compound 10 (chloroform solution).
Figure 11:
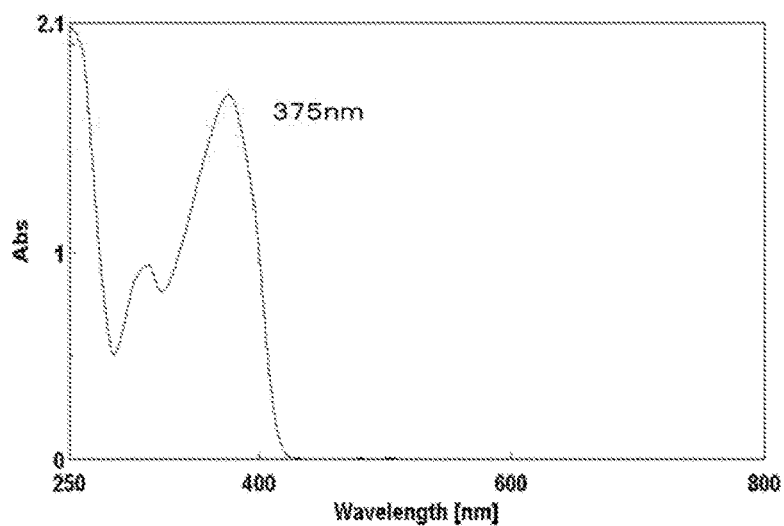
FIG. 11 is an absorption spectrum of the compound 1 (chloroform solution).
Figure 12:
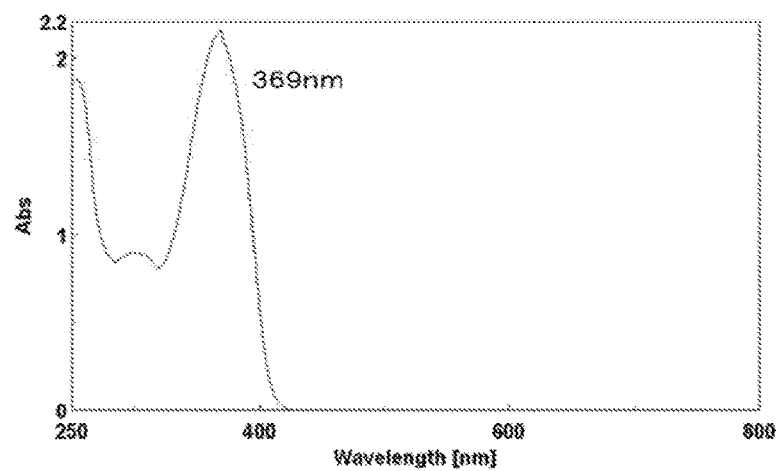
FIG. 12 is an absorption spectrum of the compound 12 (chloroform solution).
Figure 13:
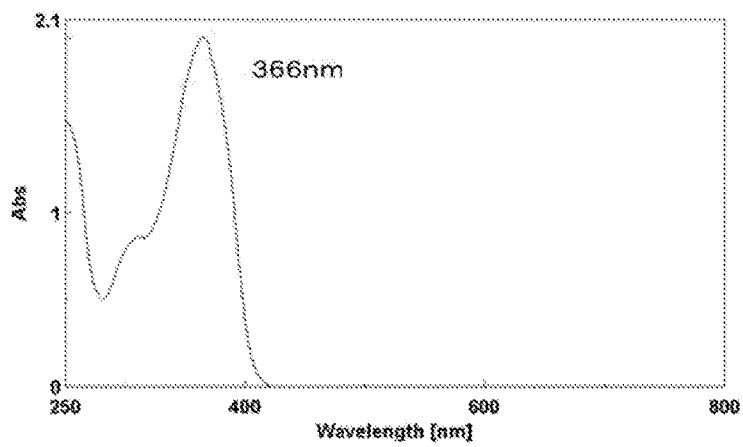
FIG. 13 is an absorption spectrum of the compound 13 (chloroform solution).
Figure 14:
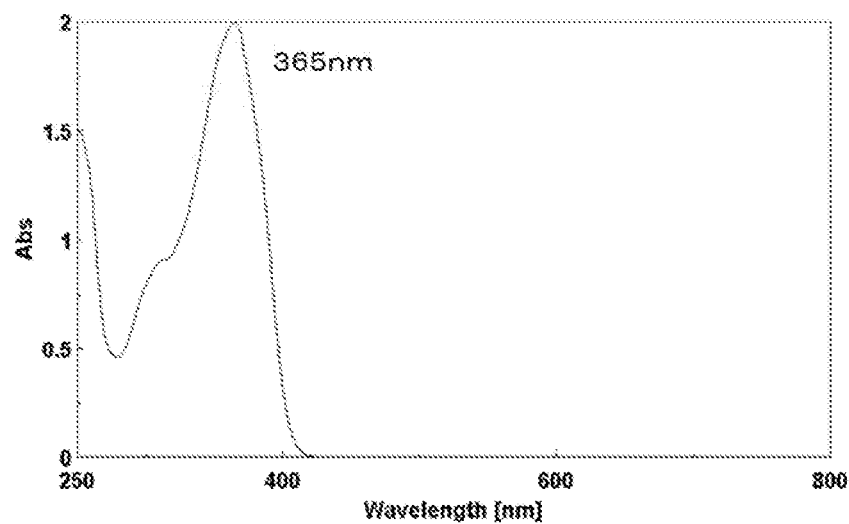
FIG. 14 is an absorption spectrum of the compound 14 (chloroform solution).
Figure 15:
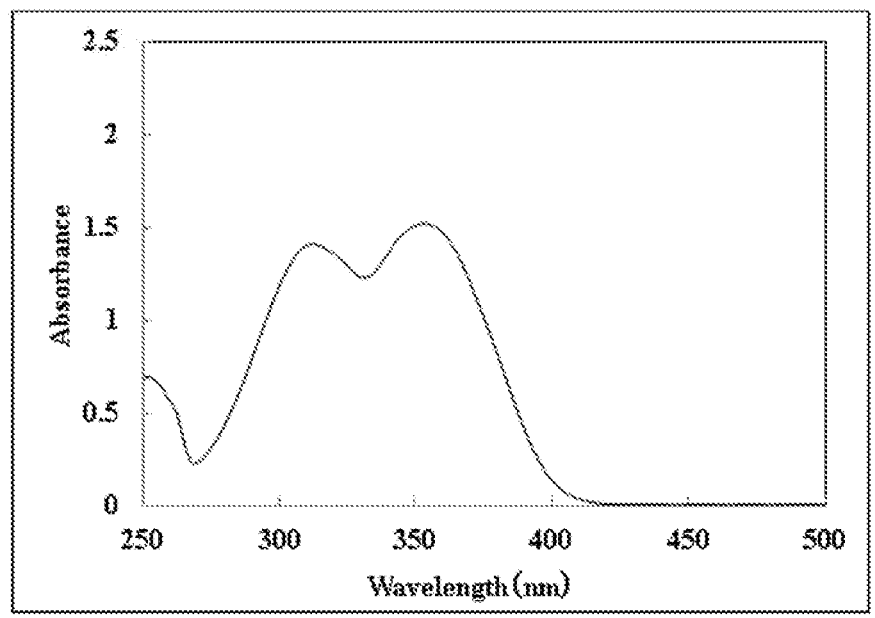
FIG. 15 is an absorption spectrum of 2-(2-hydroxy-3-t-butyl-5-methylphenyl)-chlorobenzotriazole (chloroform solution).
Figure 16:
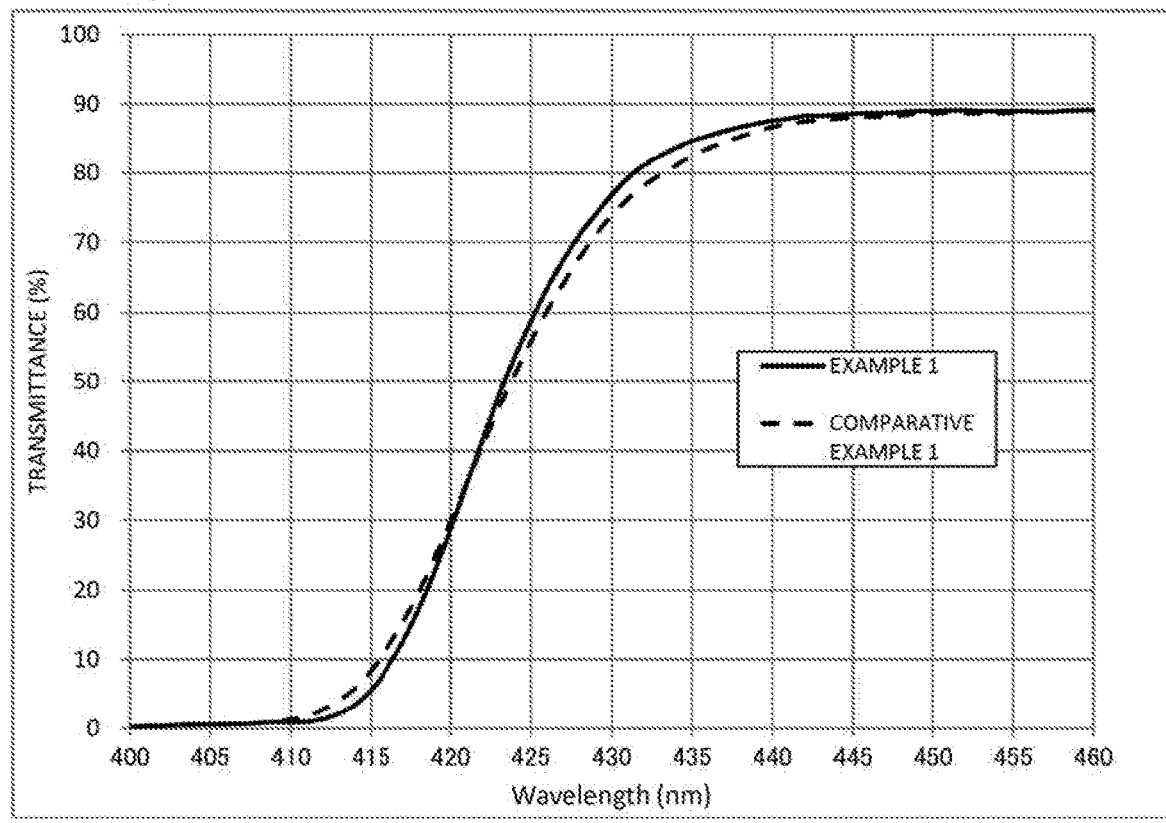
FIG. 16 is a transmission spectrum of a plastic lens of Example 1 and Comparative Example 1.
Figure 17:
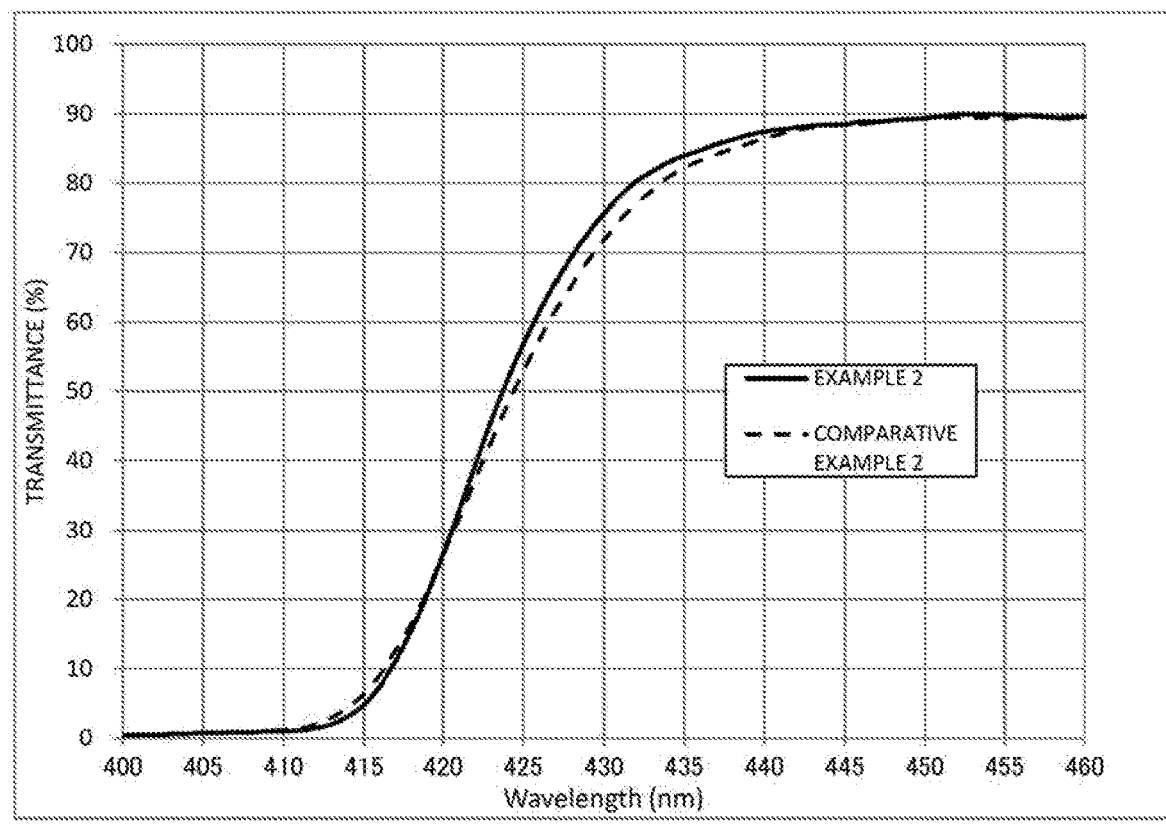
FIG. 17 is a transmission spectrum of a plastic lens of Example 2 and Comparative Example 2.
Figure 18:
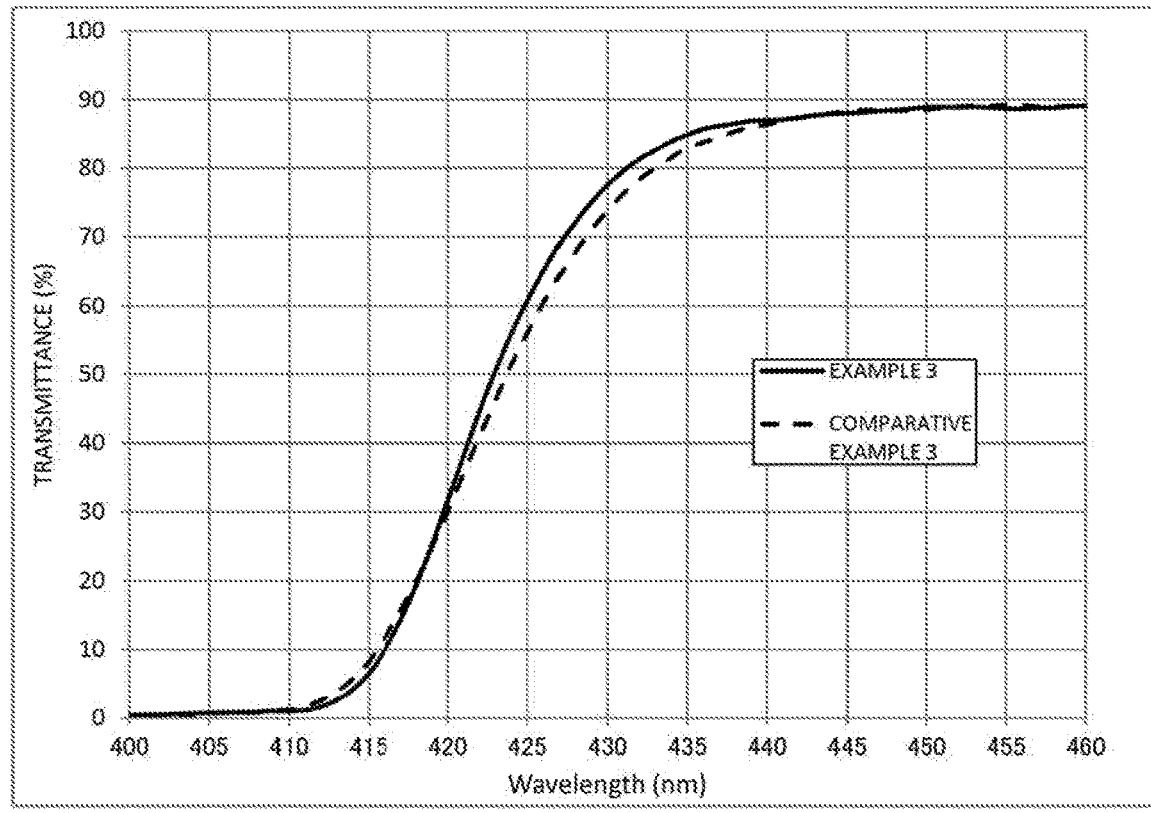
FIG. 18 is a transmission spectrum of a plastic lens of Example 3 and Comparative Example 3.
Figure 19:
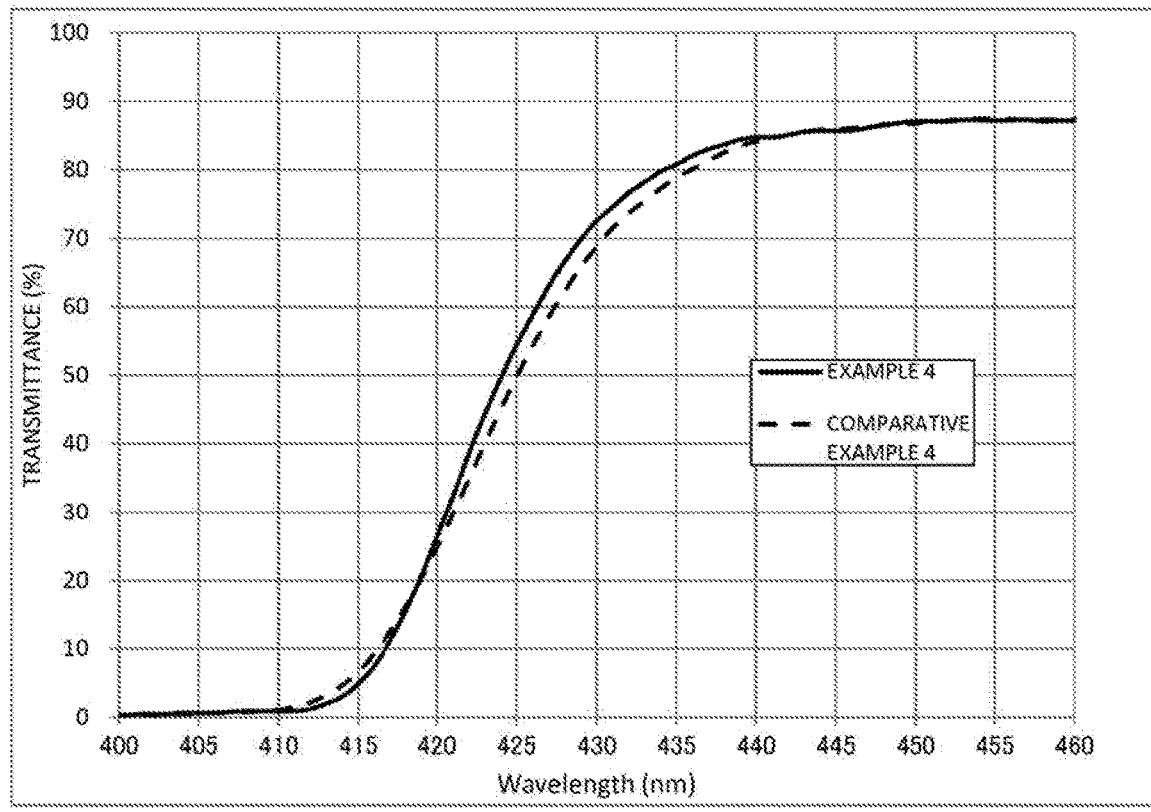
FIG. 19 is a transmission spectrum of a plastic lens of Example 4 and Comparative Example 4.
Figure 20:
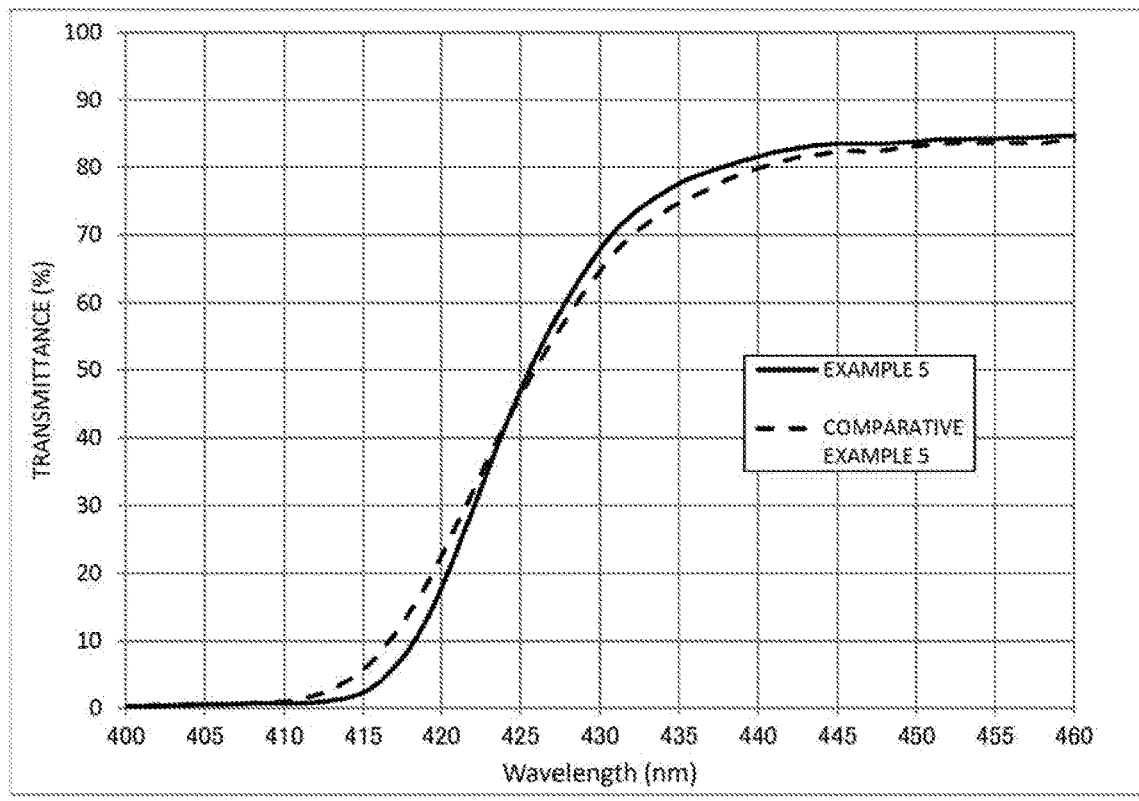
FIG. 20 is a transmission spectrum of a plastic lens of Example 5 and Comparative Example 5.
Figure 21:
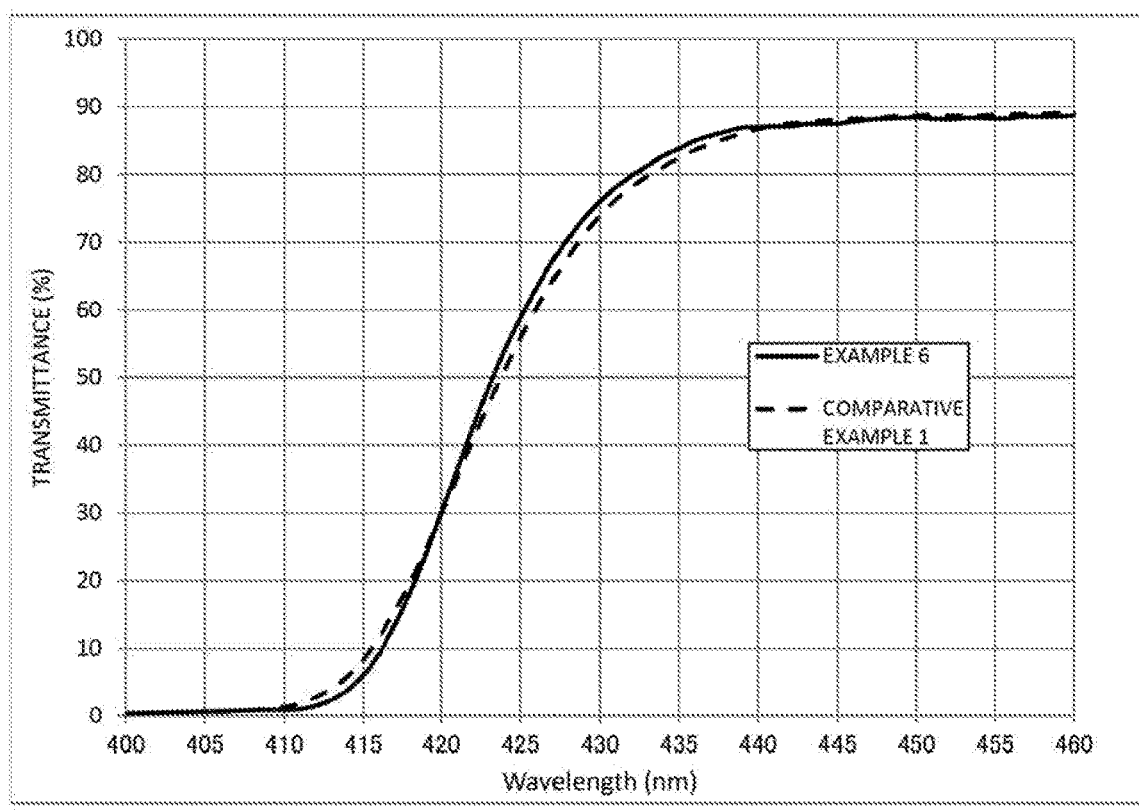
FIG. 21 is a transmission spectrum of a plastic lens of Example 6 and Comparative Example 1.

Hereinbelow, the present invention is explained in detail.
[Substituent Group and the Like]
In the present invention, the followings are included in "a monovalent group or a divalent group selected from an aromatic group, an unsaturated, group, a sulfur-containing group, an oxygen-containing group, a phosphorus-containing group, an alicyclic group, and a halogen atom".

(Aromatic Group)

The aromatic group includes an aromatic ring such as benzene ring, naphthalene ring, or anthracene ring, and it has carbon atom number of preferably 6 to 18, and more preferably 6 to 14. Examples of the monovalent or divalent aromatic group include a phenyl group, a 2-methylphenyl group, a 3-methylphenyl group, a 4-methylphenyl group, a 2,4-dimethylphenyl group, a 2,5-dimethylphenyl group, a 3,4-dimethylphenyl group, a 3,5-dimethylphenyl group, a 2,4,5-trimethylphenyl group, a 2,4,6-trimethylphenyl group, a 4-biphenyl group, a 1-naphthyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-chlorophenyl group, a 2-fluorophenyl group, a 4-fluorophenyl group, a 2-trifluoromethylphenyl group, a 4-trifluoromethylphenyl group, a 1-naphthyl group, and a 2-naphthyl group.

(Unsaturated Group)

The unsaturated group includes an unsaturated bond between a carbon-carbon or a carbon-heteroatom such as a carbon-carbon double bond, a carbon-carbon triple bond, a carbon-oxygen double bond (a carbonyl group, an aldehyde group, a carboxy group, and the like), a carbon-nitrogen double bond (an isocyanate group and the like), and a carbon-nitrogen triple bond (a cyano group, a cyanato group, and the like), and it has carbon atom number of preferably 1 to 10, and more preferably 1 to 8.

Examples of the monovalent or divalent unsaturated group include an acroyl group, a methacroyl group, a maleic acid mono ester group, a styryl group, an allyl group, a vinyl group, an amide group, a carbamoyl group, a cyano group, and an isocyanate group.

(Sulfur-Containing Group)

The sulfur-containing group includes a thiol group, a sulfide group, a disulfide group, a sulfonyl group, a sulfo group, a thiocarbonyl group, and a thiourea group, and it has carbon atom number of preferably 0 to 10. Examples of the monovalent or divalent sulfur-containing group include a thiomethoxy group, a thioethoxy group, a thio-n-propoxy group, a thioisopropoxy group, a thio-n-butoxy group, a thio-t-butoxy group, a thiophenoxy group, a p-methylthiophenoxy group, a p-methoxythiophenoxy group, a thiophene group, a thiazole group, a thiol group, a sulfo group, a sulfide group, a disulfide group, a sulfonyl group, a thiocarbonyl group, a thiourea group, a thiocarbamate group, and a dithiocarbamate group.

(Oxygen-Containing Group)

The oxygen-containing group preferably has carbon atom number of 6 to 12 when it includes an aromatic ring group or an alicyclic group, or carbon atom number of 0 to 6 when it does not include an aromatic ring group or an alicyclic group. Examples of the monovalent or divalent oxygen-containing group include a hydroxy group, a methoxy group, an ethoxy group, a propoxy group, a butoxy group, a phenoxy group, a methylphenoxy group, a dimethylphenoxy group, a naphthoxy group, a phenylmethoxy group, a phenylethoxy group, an acetoxy group, an acetyl group, an aldehyde group, a carboxy group, a urea group, an ether group, a carbonyl group, an ester group, an oxazole group, a morpholine group, and a carbamate group.

(Phosphorus-Containing Group)

The phosphorus-containing group includes a phosphine group, a phosphite group, a phosphonic acid group, a phosphinic acid group, a phosphoric acid group, and a phosphoric acid ester group. The phosphorus-containing group preferably has carbon atom number of 6 to 22 when it includes an aromatic ring group or an alicyclic group, or carbon atom number of 0 to 6 when it does not include an aromatic ring group or an alicyclic group. Examples of the monovalent or divalent phosphorus-containing group include a trimethylphosphine group a tributylphosphine group, a tricyclohexylphosphine group, a triphenylphosohine group, a tritolyiphosphine group, a methylphosphite group, an ethylphosphite group, a phenylphosphite group, a phosphonic acid group, a phosphinic acid group, a phosphoric acid group, and a phosphoric acid ester group, (Alicyclic Group)

The alicyclic group preferably has carbon atom number of 3 to 10, and, more preferably 3 to 8. Examples of the monovalent or divalent alicyclic group include a cyclopropyl group, a cyclobutyl group, a cyclopentyl group, a cyclohexyl group, a cycloheptyl group, and a cyclooctyl group.

(Halogen Atom)

Examples of the halogen atom include a fluorine atom, a chlorine atom, a bromine atom, and an iodine atom.

1. Ultraviolet absorbing agent represented by the formula (I)

The ultraviolet absorbing agent represented by the above formula (I) has, in a benzotriazole-based skeleton, the monovalent sulfur-containing group represented by the above formula (i).

In the formula (i), $R^{10}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group and a halogen atom.

Examples of the divalent hydrocarbon group for $R^{10}$ include a linear or branched alkylene group, a linear or branched alkenylene group, and a linear or branched alkynylerie group. Specific examples thereof include a methylene group, an ethane-1,2-diyl group, a propane-1,3-diyl group, a methylethane-1,2-diyl group, a butane-1,4-diyl group, a butane-1,3-diyl group, a 2-methylpropane-1,3-diyl group, a pentane-1,5-diyl group, a pentane-1,4-diyl group, a hexane-1,6-diyl group, a heptane-7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an octadecarte-1,18-diyl group, a nonadecane-1,19-diyl group, and an eicosanoic acid-1,20-diyl group. Among them, an alkylene group is preferable, and a linear alkylene group is more preferable.

In the divalent hydrocarbon group for $R^{10}$, when the hydrogen atom is substituted, at least any one of two terminals is interrupted, or carbon-carbon bond is interrupted by the aforementioned monovalent group or divalent group, number of the monovalent or divalent group is preferably 2 or less, and more preferably 1 or less.

Specific examples of an aromatic group, an unsaturated group, a sulfur-containing group, an oxygen-containing group, a phosphorus-containing group, an alicyclic group, and a halogen atom s the monovalent or divalent group include those exemplified in the section of [Substituent group and the like] above.

In the formula (i), when n is 2 or higher, $R^{11}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom.

As for the divalent hydrocarbon group for $R^{11}$, those exemplified above as the divalent hydrocarbon group for $R^{10}$ in the above can be mentioned. Among them, an alkylene group is preferable, and a linear alkylene group is more preferable.

In the divalent hydrocarbon group for $R^{11}$, when the hydrogen atom is substituted, at least any one of two terminals is interrupted, or carbon-carbon bond is interrupted by the monovalent group or the divalent group, number of the monovalent or divalent group is preferably 2 or less, and more preferably 1 or less.

Specific examples of an aromatic group, an unsaturated group, a sulfur-containing group, an oxygen-containing group, a phosphorus-containing group, an alicyclic group, and a halogen atom as the monovalent or divalent group include those exemplified in the section of [Substituent group and the like] above.

In the formula (i), $R^{12}$ represents a hydrogen atom or a group represented by $-(R^{13})_p-R^{14}$ ($R^{13}$ represents a divalent hydrocarbon group with 1 to 20 carbon atoms which may be substituted a hydrogen atom with, interrupted a proximal terminal by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom, and $R^{14}$ represents a hydrogen atom or a substituent group containing any one skeleton selected from benzotriazole, benzophenone, benzoic acid ester, and triazine. p represents an integer of 0 or 1).

As for the divalent hydrocarbon group for $R^{13}$, those exemplified above as the divalent hydrocarbon group for $R^{10}$ in the above can be mentioned. Among them, an alkylene group is preferable, and a linear alkylene group is more preferable.

In the divalent hydrocarbon group for $R^{13}$, when the hydrogen atom is substituted, a proximal terminal is interrupted, or carbon-carbon bond is interrupted by the monovalent group or the divalent group, number of the monovalent or divalent group is preferably 2 or less, and more preferably 1 or less.

Specific examples of an aromatic group, an unsaturated group, a sulfur-containing group, an oxygen-containing group, a phosphorus-containing group, an alicyclic group, and a halogen atom as the monovalent or divalent group include those exemplified in the section of [Substituent group and the like] above.

In a case in which $R^{14}$ is a substituent group containing any one skeleton selected from benzotriazole, benzophenone, benzoic acid ester, and triazine, examples of the substituent group containing benzotriazole include a group represented by the formula (A). Examples of the substituent group containing benzophenone include a group represented by the formula (B). Examples of the substituent group containing benzoic acid ester include a group represented by the formula (C). Examples of the substituent group containing triazine include a group represented by the formula (D).

[Chemical Formula 3]

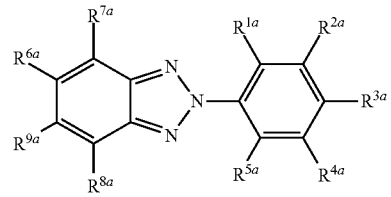

(A)

In the formula (A), any one of $R^{1a}$ to $R^{9a}$ represents a monovalent binding part which binds to $R^{13}$ of the formula (i) or the terminal sulfur atom, and $R^{1a}$ to $R^{9a}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom.

[Chemical Formula 4]

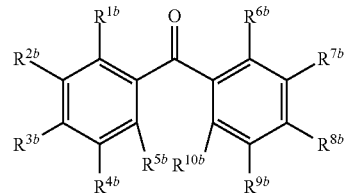

(B)

In the formula (B), any one of $R^{1b}$ to $R^{10b}$ represents monovalent binding part which binds to $R^{13}$ of the formula (i) or the terminal sulfur atom, and $R^{1b}$ to $R^{10b}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom.

[Chemical Formula 5]

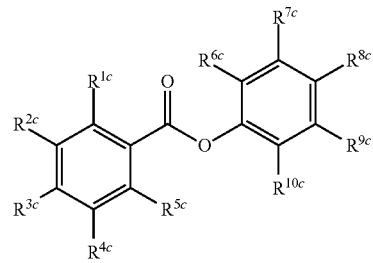

(C)

In the formula (C), any one of $R^{1c}$ to $R^{10c}$ represents a monovalent binding part which binds to $R^{13}$ of the formula (i) or the terminal sulfur atom, and $R^{1c}$ to $R^{10c}$ other than that each independent represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom.

[Chemical Formula 6]

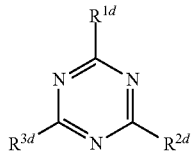

(D)

In the formula (D), $R^{1d}$ to $R^{3d}$ represents any one of the following [A] and [B].

[A] At least one of $R^{1d}$ to $R^{3d}$ represents a monovalent binding part which binds to $R^{13}$ of the formula (i) or the terminal sulfur atom, and $R^{1d}$ to $R^{3d}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, a halogen atom, and a group represented by the following formula (d):

[Chemical Formula 7]

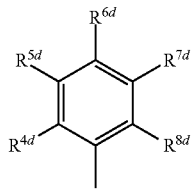

(d)

(in the formula, $R^{4d}$ to $R^{8d}$ each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom). Namely, 1 to 3 groups represented by the formula (I) may be bonded to the triazine ring.

[B] At least one of $R^{1d}$ to $R^{3d}$ represents a group represented by the following formula (d');

[Chemical Formula 8]

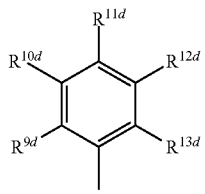

(d')

(at least one of $R^{9d}$ to $R^{13d}$ represents a monovalent binding part which binds to $R^{13}$ of the formula (i) or the terminal sulfur atom, and $R^{9d}$ to $R^{13d}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom), and $R^{1d}$ to $R^{3d}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom, Namely, 1 to 5 groups represented by the formula (I) may be bonded to the benzene ring represented by the above formula (d').

With regard to the formulae (A) to (D) and (d), when $R^{1a}$ to $R^{9a}$, $R^{1b}$ to $R^{10b}$, $R^{1c}$ to $R^{10\ c}$, and $R^{1d}$ to $R^{13d}$ are a monovalent hydrocarbon group, examples of this monovalent hydrocarbon group include a linear or branched alkyl group, a linear or branched alkenyl group, and a linear or branched alkynyl group. Specific examples thereof include a methyl group, an ethan-1-yl group, a propan-1-yl group, a 1-methylethan-1-yl group, a butan-1-yl group, a butan-2-yl group, a 2-methylpropan-1-yl group, a 2-methylpropan-2-yl group, a pentan-1-yl group, a pentan-2-yl group, a hexan-1-yl group, a heptan-1-yl group, an octan-1-yl group, a nonan-1-yl group, and a decan-1-yl group.

When $R^{1a}$ to $R^{9a}$, $R^{1b}$ to $R^{10b}$, $R^{1c}$ to $R^{10\ c}$, and $R^{1d}$ to $R^{13d}$ are a monovalent group selected from an aromatic group, an unsaturated group, a sulfur-containing group, an oxygen-containing group, a phosphorus-containing group, an alicyclic group, and a halogen atom, specific examples thereof include those exemplified in the section of [Substituent group and the like] above.

In the formula (i), m represents an interger of 0 or 1, n represents an integer of 0 to 3, and preferably 0 or 1.

Total number of carbon atoms in $R^{10}$, n number of $R^{11}$, and $R^{12}$ is 30 or less in the formula (i). In particular, considering that, by having high solubility of the ultraviolet absorbing agent represented by the formula (I) for the monomer of a plastic lens, exudation of the ultraviolet absorbing agent represented by the formula (I) can be suppressed even after processing into a plastic lens, the total number of carbon atoms in the hydrocarbon group in $R^{10}$, n number of the hydrocarbon group in $R^{11}$, and the hydrocarbon group in $R^{12}$ is preferably 18 or less, and more preferably 12 or less. In particular, it is preferable that the molecular weight of the ultraviolet absorbing agent represented by the formula (I) is 550 or less.

In the formula (I), $R^1$ to $R^8$ each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom.

When $R^1$ to $R^8$ are a monovalent hydrocarbon group, examples of this monovalent hydrocarbon group include a linear or branched alkyl group, a linear or branched alkenyl group, and a linear or branched alkynyl group. Specific examples thereof include a methyl group, an ethan-1-yl group, a propan-1-yl group, a 1-methylethan-1-yl group, a butan-1-yl group, a butan-2-yl group, a 2-methylpropan-1-yl group, a 2-methyloropan-2-yl group, a pentan-1-yl group, a pentan-2-yl group, a hexan-1-yl group, a heptan-1-yl group, an octan-1-yl group, a nonan-1-yl group, and a decan-1-yl group. Among them, a linear or branched alkyl group with carbon number of 1 to 8 is preferable.

When $R^1$ to $R^8$ are a monovalent group selected from an aromatic group, an unsaturated group, a sulfur-containing group, an oxygen-containing group, a phosphorus-containing group, an alicyclic group, and a halogen atom, specific examples thereof include those exemplified in the section of [Substituent group and the like] above.

To absorb harmful light with, a wavelength of 400 to 420 nm and suppress the absorption of light with a wavelength of around 420 nm or longer as a cause of the yellow coloration of a lens so as to provide a plastic lens with suppressed yellow coloration and excellent appearance, the ultraviolet absorbing agent of the formula (I) preferably has, in 100 μM chloroform solution, a light absorption peak present in 350 to 390 nm, more preferably in 360 to 380 nm, and particularly preferably in 360 to 375 nm. Furthermore, the absorption peak present in those wavelength ranges is preferably the maximum absorption wavelength ($\lambda_{max}$). Furthermore, with regard to the peak having that wavelength, to suppress absorption of light with a wavelength of around 420 nm or longer, the absorption spectrum at longer wavelength side is preferably as sharp as possible (i.e., higher in absolute value of gradient is better), and the gradient at longer wavelength side of the absorption peak (i.e., absolute value of gradient of a straight line connected between an absorption peak and a peak end of an absorption spectrum at longer wavelength side; FIG. 1, see Examples that will be described later) is preferably 0.025 or more, and more preferably 0.030 or more. Furthermore, to have efficient absorption with a small amount, the molar absorption coefficient maximum molar absorption coefficient: $\varepsilon_{\lambda max}$) of the above absorption peak in 350 to 390 nm is preferably 17000 L/(mol·cm) or more, more preferably 18000 L/(mol·cm) or more, and particularly preferably 20000 L/(mol·cm) or more.

To have those physical properties, the structure of the above formula (i) having $R^9$ is essential, and in particular, $R^8$ preferably has the structure of the following formula (i-1) in which a sulfur atom is directly introduced to a benzotriazole skeleton with m=0.

[Chemical Formula 9]

(i-1)

(in the formula, $R^{11}$, $R^{12}$ and n are as defined in the above).

When it is tried to cut a wavelength range of from 400 to 420 nm by using an ultraviolet absorbing agent, depending on the type of an ultraviolet absorbing agent, a yellow coloration of a resin may occur or white cloudiness of a resin may occur due to separation which is caused by insufficient dissolution in the resin of a plastic resin. For example, it is described in Patent Literature 2 that, when an ultraviolet absorbing agent with molecular weight of more than 360 is used, solubility for a raw material monomer is lowered, and even at blending amount of 5 wt % or less, separation occurs on a surface of a plastic lens, and at a limit amount for having no separation, it is difficult to obtain a plastic lens which can sufficiently absorb ultraviolet light with a wavelength of 380 to 400 nm as there is no sufficient ultraviolet absorbing property.

However, even at molecular weight of more than 360, the ultraviolet absorbing agent used in the present invention has high solubility for a plastic lens monomer due to the structural characteristic of the agent. As such, no surface exudation occurs even after processing into a plastic lens, and based on the optical characteristic, light with a wavelength range of 380 to 420 nm can be sufficiently absorbed. In addition, due to a high ultraviolet absorbing effect (i.e., high molar absorption coefficient), light with that wavelength can be sufficiently absorbed even with addition of a small amount. Furthermore, in chloroform solution, as the gradient of an absorption peak in 350 to 390 nm is higher than an ultraviolet absorbing agent of a related art, yellow coloration of a plastic lens can be suppressed.

In the plastic lens of the present invention, the addition amount of the ultraviolet absorbing agent represented by the formula (I) is preferably 0.01 to 2.0 parts by mass, more preferably 0.1 to 0.8 parts by mass, and particularly preferably 0.2 to 0.6 parts by mass relative to 100 parts by mass of a resin material. As the addition amount of the ultraviolet absorbing agent is within this range, a sufficient ultraviolet absorbing effect is obtained, and also an occurrence of a change in optical characteristics like yellow coloration or a decrease in refractive index of a lens or a lowered mechanical strength of a lens can be suppressed. In particular, according to the plastic lens of the present invention in which the ultraviolet absorbing agent represented by the formula (I) is used, Abbe's number can be high without lowering the refractive index compared to an ultraviolet absorbing agent of a related art. As such, a mode having less chromatic aberration in a lens, in particular, in an eyeglass lens, can be provided.

The resin material used for the plastic lens of the present invention is not particularly limited, and examples thereof include a thermosetting resin such as episulfide, thiourethane, urethane, epoxy, allyl, melamine, silicone, phenol, urea, or unsaturated polyester, an acrylic resin such as methyl poly(meth)acrylic acid, ethyl poly(meth)acrylic acid, or methyl (meth)acrylic acid-butyl (meth)acrylic acid copolymer, a polyolefinic resin such as polyethylene, polypropylene, polymethylpentene, or cyclic olefinic polymer, a thermoplastic polyester resin such as a polycarbonate resin, a polyethylene terephthalate, or polyethylenenaphthalate, a cellulose resin such as polyamide, polyimide, polystyrene, acrylonitrile-styrene copolymer, polyether sulfone, polysulfone, or triacetyl cellulose, a thermoplastic resin such as polyvinyl acetate, ethylene-vinyl acetate copolymer, polyvinyl pyrrolidone, polyvinyl chloride, polyvinylidene chloride, polyether ether ketone, polyacetal, nylon, or polyurethane, and an ultraviolet curable resin such as acryl, for example, a monofunctional or polyfunctional (meth)acrylate compound like 2-hydroxyethyl acrylic acid or methacrylic acid of polyalcohol or methacrylic acid ester, a polyfunctional urethane (meth)acrylate compound which is synthesized from diisocyanate and hydroxyl ester of polyalcohol and acrylic acid or methacrylic acid, polyether, polyester, epoxy, alkyd, spiroacetal, polybutadiene, or polythiolpolyene having an acrylate-based functional group. Furthermore, to the above resin composition for a plastic lens, 1 or more kinds of an ultraviolet absorbing agent other than the ultraviolet absorbing agent represented by the formula (I) may be added in combination.

According to a preferred embodiment, the plastic lens of the present invention contains an episulfide resin as a resin material, To a polymerizable composition to be a raw material of an episulfide resin, an episulfide compound is added. Examples of the episulfide compound include a chain type aliphatic 2,3-epithiopropylthio compound such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3- epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl) propane, 2,2-bis(2,3-epithiopropylthiomethyl)-1-(2,3-epithiopropylthio)butane, 1,5-bis(3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 8-bis(2,3 epithiopropylthio)-4,5-bis(2,3-epithiopropylthiomethyl)-3,6-dithiaoctane, 8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[{2-(2,3-epithiopropylthio)ethyl}thiomethyl]-2-(2,3-epithiopropylthio)ethane, 1,1,2,2-tetrakis[{2-(2,3-epithiopropylthio)ethyl}thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis (2,3-epithiopropylthiomethyl)-3,6,9-trithiaundecane, or 1,11-bis(2,3-epithiopropylthio)-5,7-bis(2,3-epithiopropylthiomethyl)-3,6,9,-trithiaundecane, a cyclic aliphatic 2,3-epithiopropylthio compound such as 1,3-bis(2,3-epithiopropylthio)cyclohexane, 1,4-bis(2,3-epithiopropylthio) cyclohexane, 3-bis(2,3-epithiopropylthiomethyl) cyclohexane, 1,4-bis(2,3-epithiopropylthiomethyl) cyclohexane, 2,5-bis(2,3-epithiopropylthiomethyl)-1,4-dithiane, 2,5-bis[{2-(2,3-epithiopropylthio) ethyl}thiomethyl]-1,4-dithiane, or 2,5-bis(2,3-epithiopropylthiomethyl)-2,5-dimethyl-1,4-dithiane, an aromatic 2,3-epithiopropylthio compound such as 1,2-bis(2,3-epithiopropylthio)benzene, 3-bis(2,3-epithiopropylthio) benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis{4-(2,3-epithiopropylthio)phenyl}methane, 2,2-bis{4-(2,3-epithiopropylthio)phenyl}propane, bis{4-(2,3-epithiopropylthio)phenyl}sulfide, bis{4-(2,3-epithiopropylthio)phenyl}sulfone, or 4,4'-bis(2,3-epithiopropylthio)biphenyl, and a mercapto group-containing epithio compound such as 3-mercaptopropylene sulfide or 4-mercaptobutene sulfide. They may be used either singly or in combination of 2 or more types.

In the above polymerizable composition, a compound in which part or all of the epithio group in the above episulfide compound is substituted with an epoxy group may be included. For the purpose of improving the resin including adjusting mainly the optical properties like refractive index, various physical properties like impact resistance and specific gravity of a resin to be obtained, and adjusting the viscosity and handling property or the like of a polymerizable composition, a resin modifier may be added. Examples of the resin modifier include epoxy compounds and amine compounds, a thiol compound, mercapto organic acids, organic acids and anhydrates, amino acids and mercaptoamines, and olefins including (meth)acrylates.

According to polymerization reaction of the above polymerizable composition by heating or keeping at room temperature in the presence or absence of a curing catalyst, an episulfide resin can be obtained. As for the curing catalyst, amines other than the resin modifier, phosphines, Lewis acids, catalysts for radical polymerization, and catalysts for cationic polymerization are commonly used. Depending on the purpose, for molding of the resin, a chain extender, a crosslinking agent, a photostabilizer, a anti-oxidant, a coloration inhibitor, a dye, filler, a release agent, an adhesive improver, a dyeing enhancer, or the like may be added similar to a molding method of a related art. Furthermore, 1 or more kinds of an ultraviolet absorbing agent other than the ultraviolet absorbing agent represented by the formula (I) may be added in combination.

According to a preferred embodiment, the plastic lens of the present invention contains a thiourethane resin as a resin material.

Examples of the monomer as a raw material of a thiourethane resin include, although not particularly limited, those containing as a main component a mixture of a polyisocyanate compound and a polythiol compound to be a thiourethane resin.

Examples of the polyisocyanate compound include an alicyclic polyisocyanate compound such as tolylene diisocyanate, diphenylmethane diisocyanate, polymeric diphenylmethane diisocyanate, tolidine diisocyanate, naphthalene diisocyanate, hexamethylene diisocyanate, isophorone diisocyanate, xylylene diisocyanate, hydrogenated xylylene diisocyanate, hydrogenated diphenylmethane diisocyanate, tetramethylxylylene diisocyanate, 2,5-bis(isocyanatemethyl)bicyclo[2.2.1]heptane, 2,6-bis(isocyanatemethyl)bicyclo[2.2.1]heptane, 3,8-bis(isocyanatemethyl)tricyclo[5.2.1.0$^{2.6}$]-decane, 3,9-bis(isocyanatemethyl)tricyclo[5.2.1.0$^{2.6}$]-decane, 4,8-bis(isocyanatemethyl)tricyclo[5.2.1.0$^{2.6}$]-decane, or 4,9-bis(isocyanatemethyl)tricyclo[5.2.1.0$^{2.6}$]-decane; an aliphatic polyisocyanate compound such as hexamethylene diisocyanate, 2,2,4-trimethylhexane diisocyanate, 2,4,4-trimethyl lysine diisocyanatomethyl ester, α,α,α',α'-tetramethylxylylene diisocyanate, bis(isocyanatomethyl)naphthalene, mesitylene triisocyanate, bis(isocyanatomethyl)sulfide, bis(isocyanatoethyl)sulfide, bis(isocyanatomethyl)disulfide, bis(isocyanatoethyl)disulfide, bis(isocyanatomethylthio)methane, bis(isocyanatoethylthio) methane, bis(isocyanatoethylthio)ethane, or bis(isocyanatomethylthio)ethane; an aromatic polyisocyanate compound such as bis(isocyanatomethyl)cyclohexane, dicyclohexylmethane-4,4'-diisocyanate, cyclohexane diisocyanate, methylcyclohexane diisocyanate, dicyclohexyl dimethylmethane isocyanate, or diphenyl sulfide-4,4'-diisocyanate; a heterocyclic polyisocyanate compound such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl) tetrahydrothiophene, 2,5-diisocyanato-1,4-dithiane, 2,5-bis (isocyanatomethyl)-1,4-dithiane, 4,5-diisocyanato-1,3-dithiolane, or 4,5-bis(isocyanatomethyl)-1,3-dithiolanes, a polyisocyante compound such as dimeric acid diisocyanate, and an aliophanate modified product, a biuret modified product, and an isocyanate modified product of those compounds.

Examples of the polythiol compound include an aliphatic thiol compound, an alicyclic thiol compound, an aromatic thiol compound, and a heterocycle-containing thiol compound. Specific examples thereof include an aliphatic polythiol compound such as methane dithiol, 1,2-ethane dithiol, 1,2,3-propanetrithiol, 2-cyclohexane dithiol, bis(2-mercaptoethyl) ether, tetrakis(mercaptomethyl)methane, (2-mercaptoethyl)sulfide, diethylene glycol bis(2-mercaptoacetate), diethylene glycol bis(3-mercaptopropionate), ethylene glycol bis(2-mercaptoacetate), ethylene glycol bis (3-mercaptopropionate), trimethylol propane tris(2-mercaptoacetate), trimethylol propane tris(3-mercaptopropionate), trimethylol ethane tris(2-mercaptoacetate), trimethylol ethane tris(3-mercaptopropionate), pentaerythritol tetrakis(2-mercaptoacetate), pentaerythritol tetrakis(3-mercaptopropionate), bis(mercaptomethyl)sulfide, bis(mercaptomethyl) disulfide, bis(mercaptoethyl)sulfide, bis(mercaptoethyl) disulfide, bis(mercaptopropyl)sulfide, bis(mercaptomethylthio)methane, bis(2-mercaptoethylthio) methane, bis(3-mercaptopropylthio)methane, 1,2-bis(mercaptomethylthio)ethane, 1,2-bis(2-mercaptoethylthio) ethane, 1,2-bis(3-mercaptopropylthio)ethane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl)methane, tetrakis-(2-mercaptoethylthiomethyl)methane, tetrakis(3-mercaptopropylthiomethyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane, and thioglycolic acid and mercaptopropionic acid ester thereof, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercaptopropionate), thio diglycolic acid bis(2-mercaptoethyl ester), thio dipropionic acid bis(2-mercaptoethyl ester), dithio diglycolic acid bis(2-mercaptoethyl ester), dithio dipropionic acid bis(2-mercaptoethyl ester), 1,3,3-tetrakis(mercaptomethylthio)propane, 1,1,2,2-tetrakis(mercaptomethylthio)ethane, 4,6-bis(mercaptomethylthio)-1,3-dithiane, tris(mercaptomethylthio)methane, 1,2-bis[(2-mercaptoethyl)thio]-3-mercaptopropane, or tris(merecaptoethylthio)methane; an aromatic polythiol compound such as 1,2-dimercaptobenzene, 1,3-dimercaptobenzene, 1,4-dimercaptobenzene, 1,2-bis(mercaptomethyl) benzene, 1,3-bis(mercaptomethyl)benzene, 1,4-bis(mercaptomethyl)benzene, 1,2-bis(mercaptoethyl)benzene, 1,3-bis (mercaptoethyl)benzene, 1,4-bis(mercaptoethyl)benzene, 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene, 2,5-toluene dithiol, 3,4-toluene dithiol, 1,5-naphthalene dithiol, or 2,6-naphthalene dithiol, and a heterocyclic polythiol compound such as 2-methylamino-4,6-dithiol-sym-triazine, 3,4-thiophene dithiol, bismuthiol, 4,6-bis(mercaptomethylthio)-1,3-dithiane, or 2-(2,2-bis(mercapitomethylthio)ethyl)-1,3-dithiethane.

The monomer as a raw material of a thiourethane resin has those polyisocyanate compounds and polythiol compounds as a main component. In the polymerizable composition containing it, 1 or more kinds of an ultraviolet absorbing agent other than the ultraviolet absorbing agent represented by the formula (I) may be used in combination. Furthermore, as additional components, other than the ultraviolet absorbing agent represented by the formula (I), an internal release agent, an infrared absorbing agent, a chain extender, a cross-linking agent, a photostabilizer, an anti-oxidant, a dispersion dye, an oil-soluble dye, a coloring agent like a pigment, a reaction catalyst, or the like may be added, for example. Furthermore, the polymerizable composition may be a resin material in which several kinds of a resin are mixed including an episulfide compound and a thiourethane compound, or a several kinds of a raw material monomer corresponding to each resin may be used. An acrylic material may be used as an ultraviolet curing resin. As an acrylic material, a monofunctional or polyfunctional (meth)acrylate compound like acrylic acid or methacrylic acid ester of polyhydric alcohol, and a polyfunctional urethane (meth) acrylate compound which is synthesized from diisocyanate and acrylic acid or methacrylic acid hydroxyl ester of polyhydric alcohol may be used. Furthermore, other than those, a polyether resin, a polyester resin, an epoxy resin, an alkyd resin, a spiroacetal resin, a polybutadiene resin, or a polythiolpolyene resin having an acrylate-based functional group may be also used.

In case of using an ultraviolet curing resin, a photopolymerization initiator is added to a monomer solution. It is sufficient for the photopolymerization initiator to generate radicals upon irradiation of ultraviolet ray. Examples thereof which may be used include acetophenones, benzoins, benzophenones, phosphine oxides, ketals, anthraquinones, and thioxanthones.

To a monomer solution, a solvent for dilution may be added, if necessary. Examples of the solvent include aromatic hydrocarbons such as toluene, xylene, cyclohexane, or cyclohexylbenzene; hydrocarbons such as n-hexane; ethers such as dibutyl ether, dimethoxymethane, dimethoxyethane, diethoxyethane, propylene oxide, dioxane, dioxolane, trioxane, tetrahydrofuran, anisole, or phenethol; ketones such as methyl isobutyl ketone, methyl butyl ketone, acetone, methyl ethyl ketone, diethyl ketone, dipropyl ketone, diisobutyl ketone, cyclopentanone, cyclohexanone, or methylcyclohexane; esters such as ethyl formate, propyl formate, n-pentyl formate, methyl acetate, ethyl acetate, methyl propionate, ethyl propionate, n-pentyl acetate, or γ-butyrolactone; cellosolves such as methyl cellosolve, cellosolve, butyl cellosolve, or cellosolve acetate; alcohols such as methanol, ethanol, or isopropyl alcohol; and water.

The molding method for obtaining the plastic lens of the present invention is not particularly limited, and examples thereof include a method in which a coating solution containing the additives of the present invention and a resin or a raw material monomer is applied to a substrate and a film is formed by heating, ultraviolet irradiation, or drying, a method in which the additives of the present invention is kneaded and mixed with a resin or a raw material monomer and molding is carried out by using an extruder or the like, and a casting polymerization method in which the additives of the present invention are dissolved in a raw material monomer, casted in a mold or a glass mold, and cured by heating, ultraviolet irradiation, or drying.

With regard to the casting polymerization, in particular, a polymerizable composition mixed with the ultraviolet absorbing agent represented by the formula (I) is injected to a glass, metal, or plastic casting mold which is hold by gasket or tape. Subsequently, according to curing by heating in a heatable device like heating in an oven or in water, the resin can be extracted. Furthermore, a treatment like annealing may be carried out for an extracted resin molded article.

With regard to the plastic lens of the present invention, it is preferable that the light transmittance measured at a thickness of 2 mm satisfies at least one of the following characteristics [1] to [3].

[1] (transmittance % at 425 nm)−(transmittance % at 415 nm) is50 or higher, or transmittance at 415 nm is 5% or lower.

[2] (transmittance % at 425 nm)–(transmittance % at 420 n) is27 or higher.

[3] [(transmittance % at 425 nm)–(transmittance % at 415 nm)]×(refractive index of resin–0.6) is 50 or higher.

Accordingly, while a higher absorbing effect is obtained in terms of transmittance at a wavelength shorter than 420 nm compared to a case in which an ultraviolet absorbing agent of a related art is used, yellow coloration of a lens caused by an influence of an ultraviolet absorbing agent can be suppressed without lowering the luminous transmittance.

Furthermore, because the plastic lens of the present invention is also excellent in heat resistance and light resistance, yellowish discoloration of a lens caused by thermal history or exposure to ultraviolet ray over a long period of time can be suppressed. Furthermore, the plastic lens of the present invention can have improved optical characteristics of a plastic lens, in particular, high Abbe's number.

With regard to the heat resistance, the thermal decomposition temperature of an ultraviolet absorbing agent (for example, 5 wt % weight loss temperature) is a physical property which is important for resin processing at extremely high temperature. In this regard, the plastic lens of the present invention has not only excellent heat resistance of an ultraviolet absorbing agent but also has excellent heat yellowing resistance under the conditions at which a lens (resin) added with the ultraviolet absorbing agent is used.

With regard to the light resistance, not only the light resistance of an ultraviolet absorbing agent but also the light yellowing resistance under the conditions at which a lens (resin) added with the ultraviolet absorbing agent is used is excellent.

The plastic lens of the present invention can be used for an eyeglass lens including a plastic eyeglass lens and a glass eyeglass lens, a contact lens, a camera lens, a projector lens, a binocular lens, and a telescope lens. In particular, because crystalline lens or retina can be protected against harmful ultraviolet ray, it is preferred for an eyeglass lens as it has excellent safety and can suppress yellow coloration of a lens. Other than a substrate of an eyeglass lens, it can be used for a film layer and a coating layer. Furthermore, it can be also used for an optical filter like a band stop filter, a band pass filter, a UV cut filter, and an IR cut filter that are related to the above uses.

EXAMPLES

Hereinbelow, the present invention is explained in greater detail by using examples. However, the present invention is not limited to those examples at all.

Synthesis Example 1

Synthesis of the Compound 1

[Chemical Formula 10]

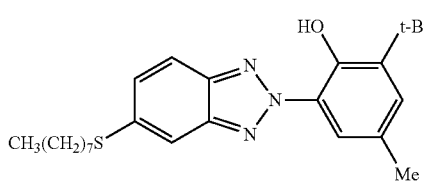

(Compound 1)

2-(2-Hydroxy-3-tert-butyl-5-methylphenyl)-5-chlorobenzotriazole (5.00 g, 15.8 mmol), octane thiol (7.63 g, 52.1 mmol), potassium carbonate (7.20 g, 52.1 mmol) and potassium iodide (0.18 g, 1.1 mmol) were reacted in 50 ml of DMF for 20 hours at 150° C. Upon the completion of the reaction, toluene was added, and according to washing, removal of solvent by distillation, and column purification, the compound 1 was obtained.

FT-IR (KBr): 3125 cm$^{-1}$; O—H stretching vibration 1438, 1391 cm$^{-1}$; triazole ring stretching vibration 661 cm$^{-1}$; C—S stretching vibration $^1$H-NMR (CDCl$_3$, 400 MHz): δ 0.88 (t, 3H, C$\underline{H}_3$(CH$_2$)$_7$—S), 1.27 (m, 8H, CH$_3$ (C$\underline{H}_2$)$_4$(CH$_2$)$_3$—S), 1.49 (m, 11H, -Ph-OH—CH$_3$—C(C$\underline{H}_3$)$_3$, CH$_3$(CH$_2$)$_4$ C$\underline{H}_2$(CH$_2$)$_2$—S), 1.75 (quin, 2H, CH$_3$ (CH$_2$)$_5$ C$\underline{H}_2$CH$_2$—S), 2.38 (s, 3H, -Ph-OH—C$\underline{H}_3$—C(CH$_3$)$_3$), 3.03 (t, 2H, CH$_3$(CH$_2$)$_5$CH$_2$C$\underline{H}_2$—S), 7.16 (s, 1H), 7.37 (d, 1H), 7.70 (s, 1H), 7.81 (d, 1H), 8.05 (s, 1H), (insg.5arom. C$\underline{H}$), 11.61 (s, 1H, -Ph-O$\underline{H}$—CH$_3$—C(CH$_3$)$_3$)

$^{13}$C-NMR (CDCl$_3$, 400 MHz): δ 14.0 ($\underline{C}$H$_3$(CH$_2$)$_7$—S), 20.0 (-Ph-OH—$\underline{C}$H$_3$—C(CH$_3$)$_3$), 22.6 (-Ph-OH—CH$_3$—$\underline{C}$(CH$_3$)$_3$), 28.7 (CH$_3$ ($\underline{C}$H$_2$)$_5$CH$_2$ CH$_2$—S), 31.9 (-Ph-OH—CH$_3$—C($\underline{C}$H$_3$)$_3$), 33.2 (CH$_3$(CH$_2$)$_5$$\underline{C}$H$_2$CH$_2$—S), 35.4 (CH$_3$(CH$_2$)$_5$CH$_2$$\underline{C}$H$_2$—S), 113.6, 117.5, 119.3, 128.7, 129.3 ($\underline{C}$H$_{arom}$), 141.2, 143.4 ($\underline{C}_{arom}$), 125.4 ($\underline{C}_{arom}$—N), 128.3 ($\underline{C}_{arom}$—CH$_3$), 138.0 ($\underline{C}_{arom}$—S), 139.1 ($\underline{C}_{arom}$—C(CH$_3$)$_3$), 146.7 ($\underline{C}_{arom}$—OH)

Synthesis Example 2

Synthesis of the Compound 2

[Chemical Formula 11]

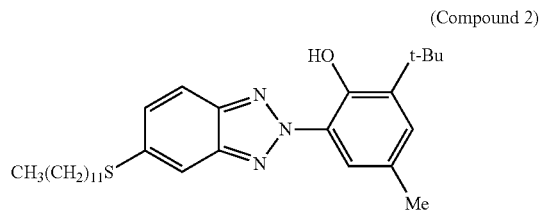

(Compound 2)

By using dodecane thiol (10.5 g, 52.1 mmol), the compound 2 was synthesized in the same manner as the compound 1. The physical property values are shown below.

FT-IR (KBr): 3009 cm$^{-1}$; O—H stretching vibration 1441, 1390 cm$^{-1}$; triazole ring stretching vibration 662 cm$^{-1}$; C—S stretching vibration $^1$H-NMR (CDCl$_3$, 400 MHz): δ 0.88 (t, 3H, C$\underline{H}_3$(CH$_2$)$_{11}$—S), 1.25 (m, 16H, CH$_3$ (C$\underline{H}_2$)$_8$(CH$_2$)$_3$—S), 1.49 (m, 11H, -Ph-OH—CH$_3$—C(C$\underline{H}_3$)$_3$, CH$_3$(CH$_2$)$_8$ C$\underline{H}_2$(CH$_2$)$_2$—S), 1.74 (quin, 2H, CH$_3$ (CH$_2$)$_9$ C$\underline{H}_2$CH$_2$—S), 2.38 (s, 3H, -Ph-OH—C$\underline{H}_3$—C(CH$_3$)$_3$), 3.03 (t, 2H, CH$_3$(CH$_2$)$_{10}$C$\underline{H}_2$—S), 7.16 (s, 1H), 7.37 (d, 1H), 7.70 (s, 1H), 7.81 (d, 1H), 8.05 (s, 1H) (insg.5arom. C$\underline{H}$), 11.61 (s, 1H, -Ph-O$\underline{H}$—CH$_3$—C(CH$_3$)$_3$)

$^{13}$C-NMR (CDCl$_3$, 400 MHz): δ 14.0 ($\underline{C}$H$_3$(CH$_2$)$_{11}$—S), 20.9 (-Ph-OH—$\underline{C}$H$_3$—C(CH$_3$)$_3$), 22.7 (-Ph-OH—CH$_3$—$\underline{C}$(CH$_3$)$_3$), 28.7~29.7 (CH$_3$ ($\underline{C}$H$_2$)$_9$CH$_2$CH$_2$—S), 31.9 (-Ph-OH—CH$_3$—C($\underline{C}$H$_3$)$_3$), 33.2 (CH$_3$(CH$_2$)$_9$$\underline{C}$H$_2$CH$_2$—S), 35.4 (CH$_3$(CH$_2$)$_9$CH$_2$$\underline{C}$H$_2$—S), 113.5, 117.5, 119.3, 128.6, 129.3 ($\underline{C}$H$_{arom}$), 141.2, 143.4 ($\underline{C}_{arom}$), 125.4 ($\underline{C}_{arom}$—N), 128.3 ($C_{arom}$—$\underline{C}H_3$), 138.0 ($\underline{C}_{arom}$—S), 139.1 ($\underline{C}_{arom}$—C(CH$_3$)$_3$), 146.7 ($\underline{C}_{arom}$—OH)

Synthesis Example 3

Synthesis of the Compound 3

[Chemical Formula 12]

(Compound 3)

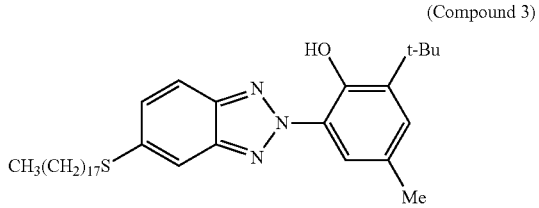

By using octadecane thiol (14.9 g, 52.1 mmol), the compound 3 was synthesized in the same manner as the compound 1. The physical property values are shown below.

FT-IR (KBr): 3059 cm$^{-1}$; O—H stretching vibration 1445, 1391 cm$^{-1}$: triazole ring stretching vibration 664 cm$^{-1}$; C—S stretching vibration $^1$H-NMR (CDCl$_3$ 400 MHz): δ 0.88 (t, 3H, C$\underline{H}_3$(CH$_2$)$_{17}$—S), 1.25 (m, 30H, CH$_3$(C$\underline{H}_2$)$_{15}$(CH$_2$)$_2$—S), 1.49 (s, 9H, -Ph-OH—CH$_3$—C(C$\underline{H}_3$)$_3$), 1.74 (quin, 2H, CH$_3$(CH$_2$)$_{15}$C$\underline{H}_2$CH$_2$—S), 2.38 (s, 3H, -Ph-OH—C$\underline{H}_3$—C(CH$_3$)$_3$), 3.03 (t, 2H, CH$_3$(CH$_2$)$_{15}$CH$_2$C$\underline{H}_2$—S), 7.16 (s, 1H), 7.37 (d, 1H), 7.70 (s, 1H), 7.81 (d, 1H), 8.05 (s, 1H) (insg.5arom. C$\underline{H}$). 11.61 (s, 1H, Ph-O$\underline{H}$—CH$_3$—C(CH$_3$)$_3$)

$^{13}$C-NMR (CDCl$_3$ 400 MHz): δ 13.1 ($\underline{C}H_3$(CH$_2$)$_{17}$—S), 19.9(-Ph-OH—$\underline{C}H_3$—C(CH$_3$)$_3$), 21.6 (-Ph-OH—CH$_3$—$\underline{C}$(CH$_3$)$_3$), 28.5($\overline{C}H_3$ ($\underline{C}H_2$)$_{16}$CH$_2$—S), 30.6($C_{arom}$—(-Ph-OH—CH$_3$—C($\underline{C}H_3$)$_3$), 34.4 (CH$_3$(CH$_2$)$_{16}$$\underline{C}$H$_2$—S), 115.5, 117.6, 118.2, 127.2, 128.0 ($\underline{C}H_{arom}$), 141.9, 142.9 ($\underline{C}_{arom}$), 124.2 ($\underline{C}_{arom}$—N), 128.1 ($\underline{C}_{arom}$—$\underline{C}H_3$) 132.3 ($\underline{C}_{arom}$—S), 140.0 ($\underline{C}_{arom}$—C(CH$_3$)$_3$), 145.6 ($\underline{C}_{arom}$—OH)

Synthesis Example 4

Synthesis of the Compound 4

Synthesis of the Intermediate 1

[Chemical Formula 13]

Br(CH$_2$)$_3$S(CH$_2$)$_7$CH$_3$ (Intermediate 1)

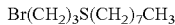

Octane thiol (29.3 g, 200 mmol) and 55% sodium hydride (13.1 g, 300 mmol) were stirred in 150 mL of THF for 2 hours under ice cooling. The obtained suspension solution was added dropwise to 100 mL of THF solution containing dibromopropane (121.1 g, 600 mmol) under ice cooling and reacted for 2 hours. After washing by adding toluene followed by distillation under reduced pressure, the intermediate 1 was obtained.

Synthesis of the Intermediate 2

[Chemical Formula 14]

HS(CH$_2$)$_3$S(CH$_2$)$_7$CH$_3$ (Intermediate 2)

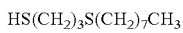

The Intermediate 1 (7.5 g, 28.2 mmol) and S-potassium thioacetate (3.4 g, 29.6 mmol) were refluxed under heating in 100 mL of acetonitrile for 6 hours. Upon the completion of the reaction, the produced solid was separated by filtration, and according to removal of solvent by distillation from the filtrate, a compound in liquid phase was obtained. Ethanol (100 mL) solution containing the obtained compound and sodium hydride (2.2 g, 55.6 mmol) was refluxed under heating for 6 hours. After cooling to room temperature, the solution was acidified by using hydrochloric acid. Toluene was added to the reaction solution, and according to washing, removal of solvent by distillation, and column purification, the intermediate 2 was obtained as liquid.

[Chemical Formula 15]

(Compound 4)

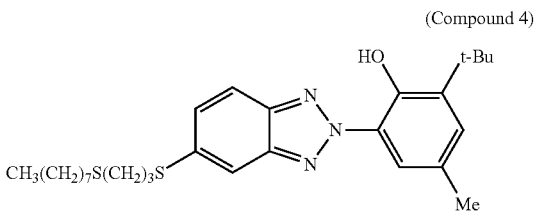

By using the intermediate 2 (11.5 g, 52.1 mmol), the compound 4 was synthesized in the same manner as the compound 1. The physical property values are shown below.

FT-IR (KBr): 3057 cm$^{-1}$; O—H stretching vibration 1437, 1391 cm$^{-1}$; triazole ring stretching vibration 664 cm$^{-1}$; C—S stretching vibration $^1$H-NMR (CDCl$_3$ 400 MHz): δ 0.81 (t, 3H, C$\underline{H}_3$(CH$_2$)$_7$—S). 1.20 (m, 8H, CH$_3$(C$\underline{H}_2$)$_4$(CH$_2$)$_3$—S), 1.30 (m, 2H CH$_3$(CH$_2$)$_4$C$\underline{H}_2$(CH$_2$)$_2$—S), 1.49 (s 9H, -Ph-OH—CH$_3$—C(C$\underline{H}_3$)$_3$), 1.54 (quin, 2H, CH$_3$(CH$_2$)$_4$CH$_2$C$\underline{H}_2$CH$_2$—S), 1.91(quin, 2H, S—CH$_2$C$\underline{H}_2$CH$_2$—S-Ph), 2.38 (s, 3H, -Ph-OH—C$\underline{H}_3$—C(CH$_3$)$_3$), 2.48 (t, 2H, CH$_3$(CH$_2$)$_4$CH$_2$CH$_2$C$\underline{H}_2$—S), 2.68 (t, 2H, S—C$\underline{H}_2$CH$_2$CH$_2$—S-Ph), 3.17 (t, 2H, S—CH$_2$CH$_2$C$\underline{H}_2$—S-Ph), 7.16 (s, 1H), 7.37 (d, 1H), 7.70 (s, 1H), 7.81 (d, 1H), 8.05 (d, 1H), (insg.5arom. C$\underline{H}$), 11.61 (s, 1H, -Ph-O$\underline{H}$—CH$_3$—C(CH$_3$)$_3$)

$^{13}$C-NMR (CDCl$_3$ 400 MHz): δ14.0 ($\underline{C}H_3$(CH$_2$)$_7$—S, 20.1(-Ph-OH—$\underline{C}H_3$—C(CH$_3$)$_3$), 22.6(-Ph-OH—CH$_3$—$\underline{C}$(CH$_3$)$_3$), 28.4(CH$_3$$\underline{C}H_2$(CH$_2$)$_6$—S), 28.9(CH$_3$(CH$_2$)$_5$$\underline{C}H_2$CH$_2$—S), 29.2(CF13(CH$_2$)$_3$$\underline{C}H_2$CH$_2$(CH$_2$)$_2$—S), 29.6 (CH$_3$(CH$_2$)$_6$$\underline{C}H_2$—S), 30.9 (S—$\underline{C}H_2$CH$_2$CH$_2$—S), 31.8 (CH$_3$CH$_2$ $\underline{C}_2$(CH$_2$)$_5$—S), 31.9(-Ph-OH—CH$_3$—C($\underline{C}H_3$)$_3$), 32.2(S—$\underline{C}H_2$CH$_2$CH$_2$—S), 35.4(S—CH$_2$CH$_2$$\underline{C}H_2$—S),114.4, 117.6, 119.3, 128.7, 129.4 ($\underline{C}H_{arom}$), 141.3, 143.3 ($\underline{C}_{arom}$), 125.4 ($\underline{C}_{arom}$—N), 128.3 ($\underline{C}_{arom}$—$\underline{C}H_3$), 137.1 ($\underline{C}_{arom}$—S), 139.1 ($\underline{C}_{arom}$—C(CH$_3$)$_3$), 146.7 ($\underline{C}_{arom}$—OH)

Synthesis Example 5

Synthesis of the Compound 5

[Chemical Formula 16]

(Compound 5)

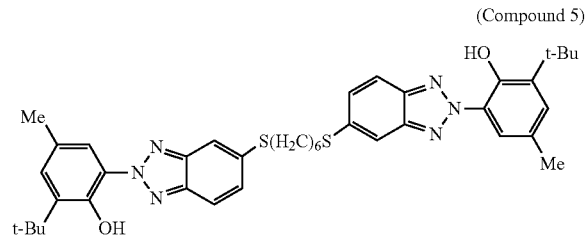

2-(2-Hydroxy-3-tert-butyl-5-methylphenyl)-5-chlorobenzotriazole (10.0 g, 31.7 mmol), hexane dithiol (4.76 g, 31.7 mmol), potassium carbonate (8.75 g, 63.3 mmol) and potassium iodide (0.37 g, 2.2 mmol) were reacted in 50 mL of DMF for 12 hours at 130° C. Upon the completion of the reaction, toluene was added to the reaction solution, and according to washing, removal of solvent by distillation, and recrystallization, the compound 5 was obtained.

FT-IR (KBr): 3009 cm$^{-1}$; O—H stretching vibration 1431, 1391 cm$^{-1}$; triazole ring stretching vibration 656 cm$^{-1}$; C—S stretching vibration $^{1}$H-NMR (CDCl$_3$ 400 MHz): δ1.49 (s, 18H, (-Ph-OH—CH$_3$—C(C$\underline{H}_3$)$_3$)$_2$), 1.55 (m, 4H, —S—CH$_2$CH$_2$C$\underline{H}_2$C$\underline{H}_2$CH$_2$CH$_2$—S—), 1.77 (m, 4H, —S—CH$_2$C$\underline{H}_2$CH$_2$CH$_2$C$\underline{H}_2$CH$_2$—S—), 2.38(s, 6H. (-Ph-OH—C$\underline{H}_3$—C(CH$_3$)$_3$)$_2$), 3.04 (t, 4H, —S—C$\underline{H}_2$CH$_2$CH$_2$CH$_2$CH$_2$C$\underline{H}_2$—S—), 7.16 (s, 2H), 7.37 (d, 2H), 7.70 (s, 2H), 7.81 (d, 2H), 8.05 (s, 2H) (insg.10arom. CH), 11.60 (s, 2H, (-Ph-O$\underline{H}$—CH$_3$—C(CH$_3$)$_3$)$_2$)

$^{13}$C-NMR (CDCl$_3$ 400 MHz): δ20.9 (-Ph-OH—$\underline{C}$H$_3$—C(CH$_3$)$_3$)$_2$, 28.4 (-Ph-OH—CH$_3$—$\underline{C}$(CH$_3$)$_3$)$_2$, 28.6 (—S—CH$_2$CH$_2$$\underline{C}$$_2$CH$_2$CH$_2$CH$_2$—S—), 29.5 (-Ph-OH—CH$_3$—C($\underline{C}$H$_3$)$_3$)$_2$, 33.1 (—S—CH$_2$CH$_2$CH$_2$CH$_2$$\underline{C}$H$_2$CH$_2$—S—), 35.4 (—S—$\underline{C}$H$_2$CH$_2$CH$_2$CH$_2$CH$_2$$\underline{C}$H$_2$—S—) 113.7, 117.6, 119.3, 128.3, 129.3, ($\underline{C}$H$_{arom}$), 141.2, 143.4 ($\underline{C}_{arom}$), 125.4 ($\underline{C}_{arom}$—N), 128.3 ($\underline{C}_{arom}$—CH3), 137.7 ($\underline{C}_{arom}$—S), 139.1 ($\underline{C}_{arom}$—C(CH$_3$)$_3$), 146.7 ($\underline{C}_{arom}$—OH)

Synthesis Example 6

Synthesis of the Compound

[Chemical Formula 17]

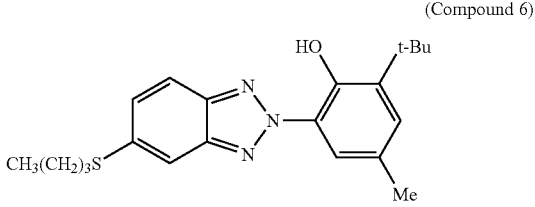

(Compound 6)

2-(2-Hydroxy-3-tert-butyl-5-methylphenyl)-5-chlorobenzotriazole (60.0 g, 0.190 mol), butane thiol (34.3 g, 0.380 mol), potassium carbonate (57.8 g, 0.418 mol), and potassium iodide (2.21 g, 0.013 mol) were reacted in 150 g of DMF for 12 hours at 125° C. Upon the completion of the reaction, pH was adjusted, and then by performing filtration, MeOH washing, washing, and recrystallization, the compound 6 was obtained.

FT-IR (KBr): 3000 cm$^{-1}$; O—H stretching vibration 1445, 1392 cm$^{-1}$; triazole ring stretching vibration 661 cm$^{-1}$; C—S stretching vibration $^{1}$H-NMR (CDCl$_3$ 400 MHz): δ 0.96 (t, 3H, C$\underline{H}_3$(CH$_2$)$_3$—S). 1.49 (m, 11H, -Ph-OH—CH$_3$—C(C$\underline{H}_3$)$_3$, CH$_3$C$\underline{H}_2$CH$_2$CH$_2$—S), 1.75 (quin, 2H, CH$_3$ CH$_2$ C$\underline{H}_2$ CH$_2$—S), 2.38 (s, 3H, -Ph-OH—C$\underline{H}_3$—C(CH$_3$)$_3$), 3.03 (t, 2H, CH$_3$CH$_2$CH$_2$C$\underline{H}_2$—S), 7.16 (s, 1H), 7.37 (d, 1H), 7.70 (s, 1H), 7.81 (d, 1H), 8.05 (d, 1H), (insg.5arom, CH), 11.61 (s, 1H, -Ph-O$\underline{H}$—CH$_3$—C(CH$_3$)$_3$) $^{13}$C-NMR (CDCl$_3$ 400 MHz): δ 13.7 ($\underline{C}$H$_3$(CH$_2$)$_3$—S), 20.9 (-Ph-OH—$\underline{C}$H$_3$—C(CH$_3$)$_3$), 22.1 (CH$_3$$\underline{C}$H$_2$CH$_2$CH$_2$—S), 29.5 (-Ph-OH—CH$_3$—C($\underline{C}$H$_3$)$_3$), 30.8 (-Ph-OH—CH$_3$—$\underline{C}$(CH$_3$)$_3$), 32.8 (CH$_3$CH$_2$$\underline{C}$H$_2$CH$_2$—S), 35.4 (CH$_3$CH$_2$CH$_2$$\underline{C}$H$_2$—S), 113.6, 117.5, 119.3, 128.7, 129.3, ($\underline{C}$H$_{arom}$), 125.4, 141.2, 143.4 ($\underline{C}_{arom}$), 128.3 ($\underline{C}_{arom}$—CH$_3$), 138.0 ($\underline{C}_{arom}$—S), 139.1 ($\underline{C}_{arom}$—C(CH$_3$)$_3$), 146.7 ($\underline{C}_{arom}$—OH)

Synthesis Example 7

Synthesis of the Compound 7

[Chemical Formula 18]

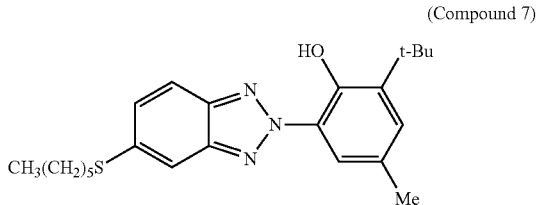

(Compound 7)

2-(2-Hydroxy-3-tert-butyl-5-methylphenyl)-5-chlorobenzotriazole (50.0 g, 0.158 mol), hexane thiol (37.4 g, 0.316 mol), potassium carbonate (48.1 g, 0.348 mol), and potassium iodide (1.8 g, 0.011 mol) were reacted in 125 g of DMF for 12 hours at 125° C. Upon the completion of the reaction, pH was adjusted, and then by performing filtration, MeOH washing, washing, and recrystallization, the compound 7 was obtained.

FT-IR (KBr): 2956 cm$^{-1}$; O—H stretching vibration 1445, 1392 cm$^{-1}$; triazole ring stretching vibration 662 cm$^{-1}$; C—S stretching vibration $^{1}$H-NMR (CDCl$_3$ 400 MHz): δ 0.89 (t, 3H, C$\underline{H}_3$(CH$_2$)$_5$—S) 1.33 (m 4H, CH$_3$ (C$\underline{H}_2$)$_2$(CH$_2$)$_3$—S), 1.49 (m, 11H, -Ph-OH—CH$_3$—C(C$\underline{H}_3$)$_3$, CH$_3$(CH$_2$)$_2$ C$\underline{H}_2$(CH$_2$)$_2$—S), 1.73 (quin, 2H, CH$_3$ (CH$_2$)$_3$ C$\underline{H}_2$CH$_2$—S), 2,38 (s, 3H, -Ph-OH—C$\underline{H}_3$—C(CH$_3$)$_3$), 3.02 (t, 2H, CH$_3$(CH$_2$)$_3$CH$_2$C$\underline{H}_2$—S), 7.16 (s, 1H), 7.36 (d, 1H), 7.69 (s, 1H), 7.78 (d, 1H), 8.04 (s, 1H), (insg.5arom. C$\underline{H}$), 11.62 (s, 1H, -Ph-O$\underline{H}$—CH$_3$—C(CH$_3$)$_3$)

$^{13}$C-NMR (CDCl$_3$ 400 MHz): δ 14.0 ($\underline{C}$H$_3$(CH$_2$)$_5$—S), 20.9 (-Ph-OH—$\underline{C}$H$_3$—C(CH$_3$)$_3$), 22.6 (CH$_3$ $\underline{C}$H$_2$(CH$_2$)$_2$CH$_2$—S), 28.7 (CH$_3$ CH$_2$ (CH$_2$)$_2$ CH$_2$CH$_2$CH$_2$—S), 29.5 (-Ph-OH—CH$_3$—C($\underline{C}$H$_3$)$_3$), 31.8 (-Ph-OH—CH$_3$—$\underline{C}$(CH$_3$)$_3$), 33.8 (CH$_3$(CH$_2$)$_2$ $\underline{C}$H$_2$CH$_2$—S), 35.4 (CH$_3$(CH$_2$)$_3$CH$_2$$\underline{C}$H$_2$—S), 113.6, 117.5, 119.3, 128.7, 129.2 ($\underline{C}$H$_{arom}$), 125.4, 141.2, 143.4 ($\underline{C}_{arom}$), 128.3 ($\underline{C}_{arom}$—CH$_3$), 138.0 ($\underline{C}_{arom}$—S), 139.1 ($\underline{C}_{arom}$—C(CH$_3$)$_3$), 146.7 ($\underline{C}_{arom}$—OH)

Synthesis Example 8

Synthesis of the Compound 8

[Chemical Formula 19]

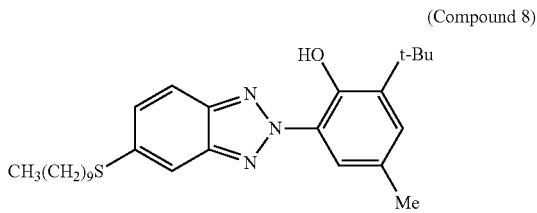

(Compound 8)

2-(2-Hydroxy-3-tert-butyl-5-methylphenyl)-5-chlorobenzotriazole (50.0 g, 0.158 mol), decanol (55.2 g, 0.317 mol), potassium carbonate (48.1 g, 0.348 mol), and potassium iodide (1.8 g, 0.011 mol) were reacted in 125 g of DMF for 12 hours at 125° C., Upon the completion of the reaction, pH was adjusted, and then by performing filtration, MeOH washing, washing, and recrystallization, the compound 8 was obtained.

FT-IR (KBr): 2958 cm$^{-1}$; O—H stretching vibration 1448, 1392 cm$^{-1}$: triazole ring stretching vibration 641 cm$^{-1}$; C—S stretching vibration $^1$H-NIMR (CDCl$_3$ 400 MHz): δ 0.89 (t, 3H, C$\underline{H}_3$(CH$_2$)$_9$—S), 1.26 (m, 12H, CH$_3$ (C$\underline{H}_2$)$_6$(CH$_2$)$_3$—S), 1.49 (m, 11H, -Ph-OH—CH$_3$—C(C$\underline{H}_3$)$_3$, CH$_3$(CH$_2$)$_6$ C$\underline{H}_2$(CH$_2$)$_2$—S), 1.74 (quin, 2H, CH$_3$ (CH$_2$)$_7$ C$\underline{H}_2$CH$_2$—S), 2.38 (s, 3H, -Ph-OH—C$\underline{H}_3$—C(CH$_3$),3), 3.03 (t, 2H, CH$_3$ (CH$_2$)$_7$CH$_2$C$\underline{H}_2$—S), 7.16 (s, 1H), 7.36 (d, 1H), 7.69 (s, 1H), 7.78 (d, 1H), 8.05 (s, 1H), (insg.5arom. C$\underline{H}$), 11.62 (s, 1H, -Ph-O$\underline{H}$—CH$_3$—C(CH$_3$)$_3$)

$^{13}$C-NMR (CDCl$_3$ 400 MHz): δ 14.0 ($\underline{C}$H$_3$(CH$_2$)$_9$—S), 20.9 (-Ph-OH—$\underline{C}$H$_3$—C(CH$_3$)$_3$), 22.7 (CH$_3$ $\underline{C}$H$_2$(CH$_2$)$_7$CH$_2$—S), 28.7~29.5 CH$_3$ CH$_2$ ($\underline{C}$H$_2$)$_6$ CH$_2$CH$_2$—S), 29.6 (-Ph-OH—CH$_3$—C($\underline{C}$H$_3$)$_3$), 31.9 (-Ph-OH—CH$_3$—$\underline{C}$(CH$_3$)$_3$), 33.1 (CH$_3$(CH$_2$)$_7$$\underline{C}$H$_2$CH$_2$—S), 35.4 (CH$_3$(CH$_2$)$_7$CH$_2$$\underline{C}$H$_2$—S), 113.6, 117.5, 119.3, 128.7, 129.3 ($\underline{C}$H$_{arom}$), 125.4, 141.2, 143.4 ($\underline{C}_{arom}$), 128.3 ($\underline{C}_{arom}$—CH$_3$), 138.0 ($\underline{C}_{arom}$—S), 139.1 ($\underline{C}_{arom}$—C(CH$_3$)$_3$), 146.7 ($\underline{C}_{arom}$—OH)

Synthesis Example 9

Synthesis of the Compound 9

[Chemical Formula 20]

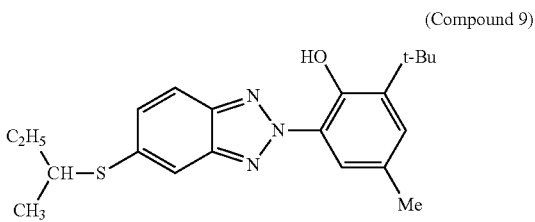

(Compound 9)

2-(2-Hydroxy-3-tert-butyl-5-methylphenyl)-5-chlorobenzotriazole (36.3 g, 0.115 mol), sec-butyl mercaptan (20.8 g, 0.231 mol), potassium carbonate (35.0 g, 0.253 mol), and potassium iodide (1.3 g, 0.008 mol) were reacted in 100 g of DMF for 12 hours at 125° C. Upon the completion of the reaction, pH was adjusted, and then by performing filtration, MeOH washing, washing and recrystallization, the compound 9 was obtained.

FT-IR (KBr): 2961 cm$^{-1}$; O—H stretching vibration 14413, 1391 cm$^{-1}$; triazole ring stretching vibration 665 cm$^-$; C—S stretching vibration $^1$H-NMR (CDCl$_3$ 400 MHz): δ 1.06 (t, 3H, C$\underline{H}_3$CH$_2$CH(CH$_3$)—S), 1.37 (d, 3H, CH$_3$CH$_2$CH(C$\underline{H}_3$)—S), 1.49 (S, 9H, -Ph-OH—CH$_3$—C(C$\underline{H}_3$)$_3$), 1.61 (m, 2H, CH$_3$C$\underline{H}_2$CH(CH$_3$)—S), 2.38 (s, 3H, -Ph-OH—C$\underline{H}_3$—C(CH$_3$)$_3$), 3.32 (m, 1H, CH$_3$CH$_2$C$\underline{H}$(CH$_3$)—S), 7.17 (s, 1H), 7.42 (d, 1H), 7.80 (s, 1H), 7.84 (d, 1H), 8.06 (d, 1H), (insg.5arom, C$\underline{H}$), 11.62 (s, 1H, -Ph-O$\underline{H}$—CH$_3$—C(CH$_3$)$_3$)

$^{13}$C-NMR (CDCl$_3$ 400 MHz): δ 11.5 ($\underline{C}$H$_3$CH$_2$CH(CH$_3$)—S), 20.3 (CH$_3$CH$_2$CH($\underline{C}$H$_3$)—S), 20.9 (-Ph-OH—$\underline{C}$H$_3$—C(CH$_3$)$_3$), 29.4 (CH$_3$$\underline{C}$H$_2$CH(CH$_3$)—S), 29.5 (-Ph-OH—CH$_3$—C($\underline{C}$H$_3$)$_3$), 35.4 (-Ph-OH—CH$_3$—$\underline{C}$(CH$_3$)$_3$), 44.6 (CH$_3$CH$_2$$\underline{C}$H(CH$_3$)—S), 117.3, 117.5, 119.3, 128.3, 128.8 ($\underline{C}$H$_{arom}$), 141.5, 143.2 ($\underline{C}_{arom}$), 125.4 ($\underline{C}_{arom}$—N), 131.2 ($\underline{C}_{arom}$—CH$_3$), 136.4 ($\underline{C}_{arom}$—S), 139.1 ($\underline{C}_{arom}$—C(CH$_3$)$_3$), 146.7 ($\underline{C}_{arom}$—OH)

Synthesis Example 10

Synthesis of the Compound 10

[Chemical Formula 21]

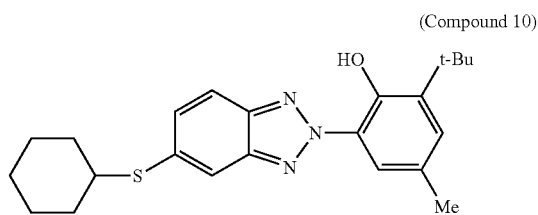

(Compound 10)

2-(2-Hydroxy-3-tert-butyl-5-methylphenyl)-5-chlorobenzotriazole (32.3 g, 0.102 mol), cyclohexane thiol (23.8 g, 0.205 mol), potassium carbonate (31.1 g, 0.225 mol), and potassium iodide (1.2 g, 0.007 mol) were reacted in 100 g of DMF for 12 hours at 125° C. Upon the completion of the reaction, pH was adjusted, and then by performing filtration, MeOH washing, washing and recrystallization, the compound 10 was obtained.

FT-IR (KBr): 2930 cm$^{-1}$; O—H stretching vibration 1450, 1391 cm$^{-1}$; triazole ring stretching vibration 667 cm$^{-1}$; C—S stretching vibration $^1$H-NMR (CDCl$_3$ 400 MHz): δ 1.40 (m, 4H, CH$_2$(C$\underline{H}_2$)$_2$(CH$_2$)$_2$CH—S), 1.49 (S, 9H, -Ph-OH—CH$_3$—C(C$\underline{H}_3$)$_3$), 1.54 (m, 2H, C$\underline{H}_2$(CH$_2$)$_2$(CH$_2$)$_2$CH—S), 1.83 (m, 2H, CH$_2$(CH$_2$)$_2$CH$_2$C$\underline{H}_2$CH—S), 2.06 (m, 2H, CH$_2$(CH$_2$)$_2$C$\underline{H}_2$CH$_2$CH—S), 2.38 (s, 3H, -Ph-OH—C$\underline{H}_3$—C(CH$_3$)$_3$), 3.29 (m, 1H, CH$_2$CH$_2$CH$_2$C$\underline{H}$—S), 7.17 (s, 1H), 7.43 (d, 1H), 7.80 (s, 1H), 7.84 (d, 1H), 8.06 (d, 1H), (insg.5arom, C$\underline{H}$), 11.62 (s, 1H, -Ph-O$\underline{H}$—CH$_3$—C(CH$_3$)$_3$)

$^{13}$C-NMR (CDCl$_3$ 400 MHz): δ 20.9 (-Ph-OH—$\underline{C}$H$_3$—C(CH$_3$)$_3$), 25.7 (CH$_2$ ($\underline{C}$H$_2$)$_2$(CH$_2$)$_2$CH—S), 26.0 ($\underline{C}$H$_2$(CH$_2$)$_2$ (CH$_2$)$_2$CH—S), 29.5 (-Ph-OH—CH$_3$—C($\underline{C}$H$_3$)$_3$), 33.1 (CH$_2$(CH$_2$)$_2$ ($\underline{C}$H$_2$)$_2$CH—S), 35.4 (-Ph-OH—CH$_3$—$\underline{C}$(CH$_3$)$_3$), 46.3 (CH$_2$(CH$_2$)$_2$ (CH$_2$)$_2$$\underline{C}$H—S), 117.2, 117.5, 119.3, 128.3, 128.8 ($\underline{C}$H$_{arom}$), 141.5, 143.2 ($\underline{C}_{arom}$), 125.4 ($\underline{C}_{arom}$—N), 131.2 ($\underline{C}_{arom}$—CH$_3$), 136.1 ($\underline{C}_{arom}$—S), 139.1 ($\underline{C}_{arom}$—C(CH$_3$)$_3$), 146.7 ($\underline{C}_{arom}$—OH)

Synthesis Example 11

Synthesis of the Compound 11

[Chemical Formula 22]

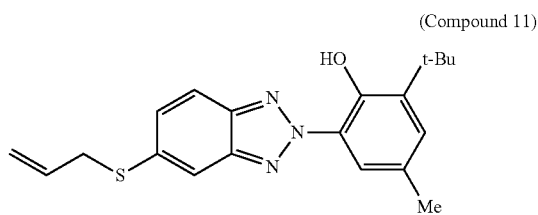

(Compound 11)

2-(2-Hydroxy-3-tert-butyl-5-methylphenyl)-5-chlorobenzotriazole (50.0 g, 0.158 mol), allyl mercaptan (23.5 g, 0.317 mol), potassium carbonate (48.1 g, 0.348 mol), and potassium iodide (1.8 g, 0.011 mol) were reacted in 125 g of DMF for 12 hours at 125° C. Upon the completion of the reaction, pH was adjusted, and then by performing filtration, MeOH washing, washing, and recrystallization, the compound 11 was obtained.

FT-IR (KBr): 3092 cm$^{-1}$; O—H stretching vibration 2999 cm$^{-1}$; =C—H stretching vibration 1449, 1390 cm$^{-1}$; triazole ring stretching vibration 664 cm$^{-1}$; C—S stretching vibration $^{1}$H-NMR (CDCl$_{3}$ 400 MHz): δ 1.49 (S, 9H, -Ph-OH—CH$_{3}$—C(CH$_{3}$)$_{3}$) 1.55 (m, 2H, CH$_{2}$=CHCH$_{2}$—S), 2.38 (s, 3H, -Ph-OH—CH$_{3}$—C(CH$_{3}$)$_{3}$), 3.38 (m, 1H, CH$_{2}$=CHCH$_{2}$—S), 3.78 (m, 1H, CH$_{2}$=CHCH$_{2}$—S), 4.23 (m, 1H, CH$_{2}$=CHCH$_{2}$—S), 7.16 (s, 1H), 7.31 (d, 1H), 7.71 (s, 1H), 7.73 (d, 1H), 8.05 (d, 1H), (insg.5arom. CH), 11.66 (s, 1H, -Ph-OH—CH$_{3}$—C(CH$_{3}$)$_{3}$)

$^{13}$C-NMR (CDCl$_{3}$ 400 MHz): δ 21.0 (-Ph-OH—CH$_{3}$—C(CH$_{3}$)$_{3}$), 22.5 (CH$_{2}$=CHCH$_{2}$—S), 29.6 (-Ph-OH—CH$_{3}$—C(CH$_{3}$)$_{3}$), 35.4 (-Ph-OH—CH$_{3}$—C(CH$_{3}$)$_{3}$), 41.8 (CH$_{2}$=CHCH$_{2}$—S), 46.3 (CH$_{2}$=CHCH$_{2}$—S), 116.7, 119.3, 123.3, 128.2, 128.6 (CH$_{arom}$), 140.8, 141.7 (C$_{arom}$), 125.4 (C$_{arom}$—N), 124.1 (C$_{arom}$—CH$_{3}$), 140.7 (C$_{arom}$—S), 139.0 (C$_{arom}$—C(CH$_{3}$)$_{3}$), 146.6 (C$_{arom}$—OH)

Synthesis Example 12

Synthesis of the Compound 12

[Chemical Formula 23]

(Compound 12)

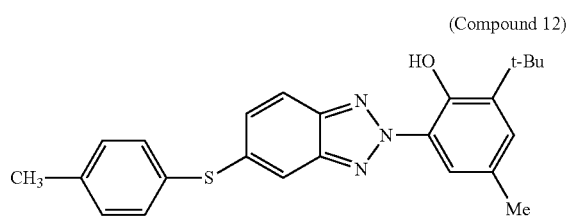

2-(2-Hydroxy-3-tert-butyl-5-methylphenyl)-5-chlorobenzotriazole (25.0 g, 79.2 mmol), p-toluene thiol (19.7 g, 158.3 mmol), potassium carbonate (24.1, 174.2 mmol), and potassium iodide (0.92 g. 5.54 mmol) were reacted in 62.5 g of DMF for 12 hours at 125° C. Upon the completion of the reaction, pH was adjusted, and then by performing filtration, MeOH washing, washing, and recrystallization, the compound 12 was obtained.

FT-IR (KBr); 3000 cm$^{-1}$; O—H stretching vibration 1444, 1389 cm$^{-1}$; triazole ring stretching vibration 667 cm$^{-1}$; C—S stretching vibration $^{1}$H-NMR (CDCl$_{3}$ 400 MHz): δ1.48 (s, 9H, -Ph-OH—CH$_{3}$—C(CH$_{3}$)$_{3}$), 2.37 (s, 3H, -Ph-OH—CH$_{3}$—C(CH$_{3}$)$_{3}$), 2.40 (s, 3H, CH$_{3}$-Ph-S—), 7.16 (s, 1H), 7.23 (s, 2H), 7.32 (d, 1H), 7.43 (s, 2H), 7.56 (s, 1H), 7.81 (d, 1H), 8.02 (d, 1H), (insg.9arom, CH), 11.56 (s, 1H, -Ph-OH—CH$_{3}$—C(CH$_{3}$)$_{3}$)

$^{13}$C-NMR (CDCl$_{3}$ 400 MHz): δ20.9 (-Ph-OH—CH$_{3}$—C(CH$_{3}$)$_{3}$), 21.2 (CH$_{3}$-Ph-S—), 29.5 (-Ph-OH—CH$_{3}$—C(CH$_{3}$)$_{3}$), 35.4 (-Ph-OH—CH$_{3}$—C(CH$_{3}$)$_{3}$), 115.3, 117.8, 119.3, 128.7, 129.3 130.5, 133.7(CH$_{arom}$), 125.4, 141.2, 143.4 (C$_{arom}$), 128.3 (C$_{arom}$—CH$_{3}$), 138.9 (C$_{arom}$—S), 138.7 (S—C$_{arom}$), 139.1 (C$_{arom}$—C(CH$_{3}$)$_{3}$), 146.7 (C$_{arom}$—OH)

Synthesis Example 13

Synthesis of the Compound 13

[Chemical Formula 24]

(Compound 13)

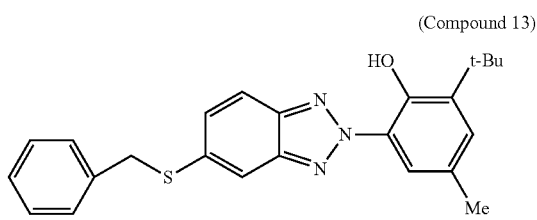

2-(2-Hdroxy-3-tert-butyl-5-methylphenyl)-5-chlorobenzotriazole (20.0 g, 63.3 mmol), benzyl mercaptan (15.7 g, 126.6 mmol), potassium carbonate (19.3 g, 139.4 mmol), and potassium iodide (0.74 g 4.5 mmol) were reacted in 50.0 g of DMF for 9 hours at 125° C. Upon the completion of the reaction, pH was adjusted, and then by performing filtration, MeOH washing, washing, and recrystallization, the compound 13 was obtained.

FT-IR (KBr): 2960 cm$^{-1}$; O—H stretching vibration 1441, 1392 cm$^{-1}$; triazole ring stretching vibration 664 cm$^{-1}$; C—S stretching vibration $^{1}$H-NMR (CDCl$_{3}$400 MHz): δ1.49 (s, 9H, -Ph-OH—CH$_{3}$—C(CH$_{3}$)$_{3}$), 2.38 (s, 3H, -Ph-OH—CH$_{3}$—C(CH$_{3}$)$_{3}$), 4.24 (s, 2H, Ph-CH$_{2}$—S—), 7.16 (s, 1H), 7.26~7.38 (m, 6H), 7.72 (s, 1H), 7.80 (d, 1H), 8.04 (d, 1H), (insg.10arom. CH), 11.58 (s, 1H, -Ph-OH—CH$_{3}$—C(CH$_{3}$)$_{3}$)

$^{13}$C-NMR (CDCl$_{3}$400 MHz): δ20.9 (-Ph-OH—CH$_{3}$—C(CH$_{3}$)$_{3}$), 29.5 (-Ph-OH—CH$_{3}$—C(CH$_{3}$)$_{3}$), 35.4 (-Ph-OH—CH$_{3}$—C(CH$_{3}$)$_{3}$), 38.6 (Ph-CH$_{2}$—S—), 115.4, 117.6, 119.3, 128.7, 128.8, 128.8, 129.7, 137.0 (CH$_{arom}$), 125.4, 141.4, 143.4 (C$_{arom}$), 128.3 (C$_{arom}$—CH$_{3}$), 136.5 (C$_{arom}$ CH$_{2}$—S—), 138.7 (S—C$_{arom}$), 139.1 (C$_{arom}$—C(CH$_{3}$)$_{3}$), 146.7 (C$_{arom}$—OH)

Synthesis Example 14

Synthesis of the Compound 14

[Chemical Formula 25]

(Compound 14)

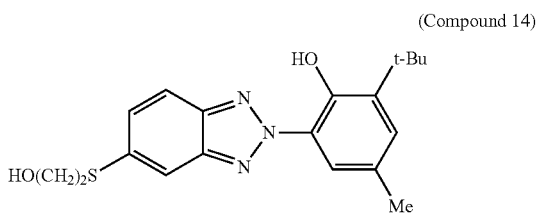

2-(2-Hydroxy-3-tert-butyl-5-methylphenyl)-5-chlorobenzotriazole (50.5 g, 0.160 mol), 2-mercaptoethanol (25.0 g, 0.320 mol), potassium carbonate (48.6 g, 0.352 mol), and potassium iodide (1.9 g. 0.011 mol) were reacted in 125 g of DMF for 12 hours at 125° C. Upon the completion of the reaction, pH was adjusted, and then by performing filtration, MeOH washing, washing, and recrystallization, the compound 14 was obtained.

FT-IR (KBr): 3350 cm$^{-1}$; O—H stretching vibration 1437, 1392 cm$^{-1}$; triazole ring stretching vibration 666 cm$^{-1}$; C—S stretching vibration $^1$H-NMR (CDCl$_3$ 400 MHz): δ 1.49 (S, 9H, -Ph-OH—CH$_3$—C(C$\underline{H}_3$)$_3$), 2.38 (s, 3H, -Ph-OH—C$\underline{H}_3$—C(CH$_3$)$_3$), 2.79 (t, 2H, HOCH$_2$C$\underline{H}_2$—S), 3.25 (t, 2H, HOC$\underline{H}_2$CH$_2$—S), 7.17 (s, 1H), 7.41 (d, 1H), 7.83 (s, 1H), 7.84 (d, 1H), 8.05 (d, 1H), (insg.5arom. C$\underline{H}$), 11.56 (s, 1H, -Ph-O$\underline{H}$—CH$_3$—C(CH$_3$)$_3$)

$^{13}$C-NMR (CDCl$_3$ 400 MHz): δ 20.9 (-Ph-OH—$\underline{C}$H$_3$—C(CH$_3$)$_3$), 29.5 (-Ph-OH—CH$_3$—C($\underline{C}$H$_3$)$_3$), 35.4 (-Ph-OH—CH$_3$—$\underline{C}$(CH$_3$)$_3$), 36.8 (HOCH$_2\underline{C}$H$_2$—S), 60.3 (HO$\underline{C}$H$_2$CH$_2$—S), 115.8, 118.0, 119.3, 128.4, 129.7 ($\underline{C}$H$_{arom}$), 141.5, 143.2 ($\underline{C}_{arom}$), 125.3 ($\underline{C}_{arom}$—N) 128.9 ($\underline{C}_{arom}$—CH$_3$), 135.7 ($\underline{C}_{arom}$—S), 139.2 ($\underline{C}_{arom}$—C(CH$_3$)$_3$), 146.7 ($\underline{C}_{arom}$—OH)

Ultraviolet Absorption

The compounds 1 to 4 and 6 to 14 were dissolved in chloroform to 100 μM, collected in a 10 mm quartz cell, and by using an ultraviolet visible spectrophotometer (V-550, manufactured by JASCO Corporation), an absorption spectrum of from 200 to 700 nm was measured. With regard to the compound 5, the absorption was outside the measurement range due to high molar absorption coefficient when the measurement is made at 100 μM. As such, the measurement was made at a concentration of 50 μM. As a comparison, a sample obtained by dissolving 2-(2-hydroxy-3-t-butyl-5-methylphenyl)-chlorobenzotriazole in chloroform in the same manner as above was also subjected to the absorption spectrum measurement (FIGS. 1 to 15). From those spectra, an absorption peak present in a wavelength range of from 350 to 390 nm (maximum absorption wavelength: $\lambda_{max}$) and absorbance were obtained, and the molar absorption coefficient (maximum molar absorption coefficient: $\varepsilon_{max}$) of that peak was obtained based on the following equation (Table 1).

Molar absorption coefficient: $\varepsilon_{max}$ (L/(mol·cm)=A: Absorbance/[c: Molar concentration (mol/L)×l: light path length of cell (cm)]

Furthermore, from the obtained absorption spectrum, the cross point between the absorption spectrum at longer wavelength side of an absorption peak present in 350 to 390 nm and the base line (i.e., line with gradient of 0 in an absorption spectrum of 430 to 500 nm) was set as a peak end (FIG. 1), and then, according to the following equation, the absolute value of gradient at longer wavelength side of an absorption peak present in wavelength range of from 350 to 390 nm was obtained (Table 2).

|Gradient at longer wavelength side of absorption peak present in wavelength range of from 350 to 390 nm|=|[(Absorbance of peak end)−(Absorbance of absorption peak present in wavelength range of from 350 to 390 nm)]/[(Absorption wavelength of peak end)−(Wavelength of absorption peak present in wavelength range of from 350 to 390 nm)]|

Furthermore, with regard to the compound 5, the absorption was outside the measurement range due to high molar absorption coefficient when the measurement is made at 100 μM. As such, the measurement was made at a concentration of 10, 25, and 50 μM, and then a graph of the absolute value of gradient at longer wavelength side of an absorption peak present in a wavelength range of from 350 to 390 nm and the concentration of ultraviolet absorbing agent was plotted. As a result, they were found to be in a linear primary relationship as shown in FIG. 23. From the formula of the graph (Y=0.0006X−0.0024), the absolute value of gradient for compound 5 at 100 μM was calculated.

TABLE 1

| | Molecular weight g/mol | Wavelength of absorption peak present in wavelength range of from 350 to 390 nm (Maximum absorption wavelength: $\lambda_{max}$) nm | Molar absorption coefficient of peak described on left side (Maximum molar absorption coefficient: $\varepsilon_{max}$) L/(mol · cm) |
|---|---|---|---|
| Compound 1 | 426 | 367.5 | 21400 |
| Compound 2 | 482 | 367.5 | 20900 |
| Compound 3 | 566 | 367.0 | 20800 |
| Compound 4 | 500 | 366.0 | 20400 |
| Compound 5 | 709 | 367.0 | 43100 |
| Compound 6 | 370 | 367.0 | 22200 |
| Compound 7 | 398 | 367.0 | 22200 |
| Compound 8 | 454 | 367.5 | 22300 |
| Compound 9 | 369 | 367.0 | 21100 |
| Compound 10 | 396 | 367.5 | 21100 |
| Compound 11 | 353 | 375.0 | 18000 |
| Compound 12 | 404 | 369.0 | 21500 |
| Compound 13 | 404 | 366.0 | 20100 |
| Compound 14 | 357 | 365.0 | 20000 |
| 2-(2-Hydroxy-3-t-butyl-5-methylphenyl)-chlorobenzotriazole | 316 | 353.5 | 15300 |

TABLE 2

|  | Absorbance of absorption peak present in wavelength range of from 350 to 390 nm | Absorbance of peak end | Absorption wavelength of peak end nm | Absolute value of gradient at longer wavelength side of absorption peak present in wavelength range of from 350 to 390 nm |
|---|---|---|---|---|
| Compound 1 | 2.13704 | 0.00147 | 426.0 | 0.0365 |
| Compound 2 | 2.09328 | 0.00089 | 426.0 | 0.0358 |
| Compound 3 | 2.08832 | 0.00909 | 424.0 | 0.0365 |
| Compound 4 | 2.05024 | 0.00023 | 425.5 | 0.0345 |
| Compound 5 | — | — | — | 0.0576 |
| Compound 6 | 2.21603 | 0.00386 | 427.0 | 0.0369 |
| Compound 7 | 2.22070 | 0.00672 | 428.0 | 0.0363 |
| Compound 8 | 2.23486 | 0.01192 | 428.0 | 0.0367 |
| Compound 9 | 2.10722 | 0.02561 | 425.0 | 0.0359 |
| Compound 10 | 2.10625 | 0.00768 | 426.0 | 0.0359 |
| Compound 11 | 1.80483 | 0.00722 | 430.0 | 0.0327 |
| Compound 12 | 2.14986 | 0.00429 | 426.5 | 0.0373 |
| Compound 13 | 2.00816 | 0.00089 | 425.0 | 0.0340 |
| Compound 14 | 1.99878 | 0.00364 | 425.0 | 0.0333 |
| 2-(2-Hydroxy-3-t-butyl-5-methylphenyl)-chlorobenzotriazole | 1.52567 | 0.00517 | 423.0 | 0.0219 |

Compared to 2-(2-hydroxy-3-t-butyl-5-methylphenyl)-chlorobenzotriazole, the ultraviolet absorbing agent of the compounds 1 to 14 has the maximum absorption wavelength present in 360 to 375 nm, high molar absorption coefficient (high ultraviolet absorption efficiency), i.e., 20000 (mol·cm) or higher for the compounds 1 to 10 and 12 to 14, and 18000 L/(mol·cm) for the compound 11, and high absolute value of gradient at longer wavelength side of the absorption peak, i.e., 0.030 or higher, thus showing sharpness.

Based on the above characteristics, it was confirmed that, according to addition of a small amount of the ultraviolet absorbing agent of the present invention to a plastic lens, absorption of light with a wavelength of around 420 nm or longer was suppressed while harmful light with a wavelength of around 400 to 420 nm was efficiently absorbed, and thus the effect of suppressing yellow coloration of a plastic lens is exhibited in the following Examples 1 to 10.
(Production of Plastic Lens)

Resins added with the ultraviolet absorbing agent of the present invention or an ultraviolet absorbing agent of a related art were prepared. Incidentally, in the following Examples and Comparative Examples, the addition amount of each ultraviolet absorbing agent was adjusted such that 420 nm transmittance of a flat lens with 2 mm thickness has a value that is as close as possible for each resin of the same material type.

Example 1

In a flask, 0.49 g of the compound 1, 0.1 g of Zelec UN manufactured by Stepan Co., Ltd., and 0.04 g of dibutyltin dichloride were added to 50.8 g of a mixture of 2,5-bis (isocyanatomethyl)-bicyclo[2,2,1]heptane and 2,6-bis(isocyanatomethyl)-bicyclo[2,2,1]heptane, and completely dissolved by stirring for 1 hour at 25° C. After that, 22.4 g of pentaerythritol tetrakis(3-mercaptopropionate) and 26.8 g of 1,2-bis[(2-mercaptoethyl)thio]-3-mercaptopropane were added to the mixture solution and stirred for 30 minutes at 25° C. Incidentally, in the combined solution, the compound 1 was contained at 0.49% by weight relative to the total weight of the polymerizable compound.

The combined solution was degassed for 1 hour at 0.3 mmHg or lower, and after performing filtration using a 5 μm PTFE filter, injected to a mold frame which consists of two flat glass plates with diameter of 80 mm of having 2 mm space and tape. Temperature of the mold was gradually raised from 25° C. to 130° C., and after being maintained for 2 hours at 130° C., cooled to room temperature. The time from the start of temperature raise to the cooling was 18 hours. Upon the completion of the polymerization, the obtained resin was released from the mold and the resulting flat lens was subjected to annealing for 2 hours at 130° C.

Example 2

A flat lens with 2 mm thickness was obtained in the same manner as Example 1 except that the compound 1 of Example 1 is added in an amount of 0.53 g (i.e., 0.53% by weight relative to the total weight of the polymerizable compound).

Example 3

To a flask, 0.53 g of the compound 1 (i.e., 0.53% by weight relative to the total weight of the polymerizable compound), 0.1 g of Zelec UN man factored by Stepan Co., Ltd., 0.2 g of dibutyl tin dichloride, and 58.9 g of dicyclohexylmethane-4,4'-diisooyanate were added, and completely dissolved by stirring for 1 hour at 25° C. After that, 41.1 g of a mixture which contains, as a main component, 5.7-dimercaptomethyl-1,11-dimercapto-3,6,9-trithiaundecane, 4.7-dirnercaptomethyl-1,11-dimercapto-3,6,9-trithiaundecane, and 4.8-dimercaptomethyl-1,11-dimercapto-3,6, 9-trithiaundecane, was added to the above mixture solution and mixed for 30 minutes at 25° C.

A flat lens with 2 mm thickness was obtained in the same manner as Example 1 except the preparation of combined solution.

Example 4

To a flask, 0.27 g of the compound 1 (i.e., 0.27% by weight relative to the total weight of the polymerizable compound), 0.1 g of Zelec UN manufactured by Stepan Co., Ltd., 0.006 g of dibutyltin dichloride, and 50.6 g of m-xylylenediisocyanate were added, and completely dissolved by stirring for 1 hour at 25° C. After that, 49.4 g of a mixture which contains, as a main component, 5.7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, was added to the above mixture solution and mixed for 30 minutes at 25° C.

A flat lens with 2 mm thickness was obtained in the same manner as Example 1 except the preparation of combined solution.

Example 5

To a flask, 0.23 g of the compound 1 (i.e., 0.23% by weight relative to the total weight of the polymerizable compound), 71 g of bis(β-epithiopropyl)sulfide, 23 g of sulfur, and 2.2 g of (2-mercaptoethyl)sulfide were added, and stirred for 30 minutes at 60° C. Subsequently, 0.14 g of 2-mercapto-1-methylimidazole was added, and after degassing for 10 minutes, at 0.3 mmHg or lower, it was stirred again for 120 minutes at 60° C. followed by cooling to 30° C. over 40 minutes. To the obtained solution, a solution obtained by dissolving 0.012 g of triethyl benzyl ammonium chloride and 0.01 g of dibutyltin dichloride in 3.8 g of (2-mercaptoethyl)sulfide was added dropwise and degassed for 20 minutes at 0.3 mmHg or lower. The resulting solution was subjected to filtration using a 5 μm PTFE filter, injected to a mold frame which consists of two flat glass plates with diameter of 80 mm of having 2 mm space and tape. Temperature of the mold was gradually raised from 25° C. to 110° C., and after being maintained for 2 hours at 110° C., cooled to room temperature. The time from the start of temperature raise to the cooling was 18 hours. Upon the completion of the polymerization, the obtained resin was released from the mold and the resulting flat lens was subjected to annealing for 2 hours at 110° C.

Example 6

A flat lens with 2 mm thickness was obtained in the same manner as Example 1 except that the compound 1 of Example 1 is changed to the compound 2 and added in an amount of 0.56 g (i.e., 0.56% by weight relative to the total weight of the polymerizable compound).

Example 7

A flat lens with 2 mm thickness was obtained in the same manner as Example 1 except that the compound 1 of Example 1 is changed to the compound 4 and added in an amount of 0.58 g (i.e., 0.58% by weight relative to the total weight of the polymerizable compound).

Example 8

A flat lens with 2 mm thickness was obtained in the same manner as Example 1 except that the compound 1 of Example 1 is changed to the compound 6 and added in an amount of 0.43 g.

Example 9

A flat lens with 2 mm thickness was obtained in the same manner as Example 1 except that the compound 1 of Example 1 is changed to the compound 7 and added in an amount of 0.47 g.

Example 10

A flat lens with 2 mm thickness was obtained in the same manner as Example 1 except that the compound 1 of Example 1 is changed to the compound 8 and added in an amount of 0.53 g.

Comparative Example 1

A flat lens with 2 mm thickness was obtained in the same manner as Example 1 except that the compound 1 of Example 1 is changed to 2-(2-hydroxy-3-t-butyl-5-methylphenyl)-chlorobenzotriazole and added in an amount of 0.75 g (i.e., 0.75% by weight relative to the total weight of the polymerizable compound).

Comparative Example 2

A flat lens with 2 mm thickness was obtained in the same manner as Example 1 except that the compound 1 of Comparative Example 1 is added in an amount of 0.85 g (i.e., 0.85% by weight relative to the total weight of the polymerizable compound).

Comparative Example 3

A flat lens with 2 mm thickness was obtained in the same manner as Example 1 except that the compound 1 of Example 3 is changed to 2-(2-hydroxy-3-t-butyl-5-methylphenyl)-chlorobenzotriazole and added in an amount of 0.75 g (i.e., 0.75% by weight relative to the total weight of the polymerizable compound).

Comparative Example 4

A flat lens with 2 mm thickness was obtained in the same manner as Example 1 except that the compound 1 of Example 4 is changed to 2-(2-hydroxy-3-t-butyl-5-methylphenyl)-chlorobenzotriazole and added in an amount of 0.50 g (i.e., 0.50% by weight relative to the total weight of the polymierizable compound).

Comparative Example 5

A flat lens with 2 mm thickness was obtained in the same manner as Example 5 except that the compound 1 of Example 5 is changed to 2-(2-hydroxy-3-t-butyl-5-methylphenyl)-chlorobenzotriazole and added in an amount of 0.30 g (i.e., 0.30% by weight relative to the total weight of the polymerizable compound).

(1) Transmittance, yellowness degree (YI value), and luminous transmittance

The sample lens produced in Examples and Comparative Examples was measured for spectrophotometric transmittance in 350 to 800 nm, yellowness degree (YI value), and luminous transmittance by using an ultraviolet visible spectrophotometer (U-4100, manufactured by Hitachi High-Technologies Corporation). The yellowness degree and luminous transmittance were the value of D65 2 degree field of view.

(2) Evaluation of appearance of sample lens

Determination of the sample lens produced above was carried out by comparing with a naked eye the yellowness degree of the sample lens of Examples and the sample lens of Comparative Examples which have close transmittance near 420 nm for a resin made of the same material. That is because, as the intrinsic yellowness degree of a resin itself varies depending on the type of a resin, it is impossible to accurately compare the yellowness degree of other resin after adding an ultraviolet absorbing agent thereto. The lens used for comparison was as follows in detail: Example 1 and Comparative Example 1, Example 2 and Comparative Example 2, Example 3 and Comparative Example 3, Example 4 and Comparative Example 4, Example 5 and Comparative Example 5, Example 6 and Comparative Example 1, Example 7 and Comparative Example 2, Example 8 and Comparative Example 1, Example 9 and Comparative Example 1, and Example 10 and Comparative Example 1. The appearance was evaluated based on the following criteria. Furthermore, exudation of the ultraviolet absorbing agent from a resin and transparency were determined with a naked eye.

Yellowness degree . . . ◯: near colorless, x: yellow (3) Refractive index and Abbe's number of resin The refractive index and Abbe's number at 546 nm of the sample lens produced above were measured by using an Abbe refractometer (DR-M4, manufactured by ATAGO CO., LTD.).

(4) Heat resistance and light resistance

[Heat Resistance Evaluation 1]

The sample lens which has been prepared in the same method as the aforementioned for above Examples and Comparative Examples except that the flat lens is prepared to 5 mm thickness was placed for 1 week in an oven heated at 60° C. After that, the lens was cooled to room temperature and YI value thereof was measured and the degree of deterioration (i.e., yellowish discoloration) of a lens was determined as ΔYI=(YI after heating)−(YI before heating) (Examples 1, 3, 4, and 5 and Comparative Examples 1, 3, 4, and 5).

[Heat Resistance Evaluation 2]

The sample lens which has been prepared in the same method as the aforementioned for above Examples and Comparative Examples except that the flat lens is prepared to 5 mm thickness was placed for 1 hour in an oven heated at 150° C. After that, the lens was cooled to room temperature and YI value thereof was measured and the degree of deterioration (i.e., yellowish discoloration) of a lens was determined as ΔYI=(YI after heating)−(YI before heating) (Example 3 and Comparative Example 3).

[Light Resistance Evaluation 1]

The sample lens with thickness of 2 mm thickness which has been prepared in Examples 1 and 3 and Comparative Examples 1 and 3 was measured for YI value of a lens after irradiation for 100 hours with light using a xenon irradiation device, and the degree of deterioration (i.e., yellowish discoloration) of a lens was determined as ΔYI (YI after xenon irradiation)−(YI before xenon irradiation).

[Light Resistance Evaluation 2]

The sample lens with thickness of 2 mm thickness which has been prepared in Examples 4 and 5 and Comparative Examples 4 and 5 was measured for YI value of a lens after irradiation for 20 hours with light using a xenon irradiation device, and the degree of deterioration (i.e., yellowish discoloration) of a lens was determined as ΔYI (YI after xenon irradiation)−(YI before xenon irradiation).

Results of the transmittance, difference in transmittance, YI value, luminous transmittance, appearance evaluation, refractive index, Abbe's number, heat resistance, and light resistance are shown in Table 3, and the results of measuring transmission spectrum are shown in FIGS. 16 to 22.

TABLE 3

|  | Example 1 | Comparative Example 1 | Example 2 | Comparative Example 2 | Example 3 | Comparative Example 3 | Example 4 | Comparative Example 4 |
| --- | --- | --- | --- | --- | --- | --- | --- | --- |
| Type of ultraviolet absorbing agent | Compound 1 | 2-(2-Hydroxy-3-t-butyl-5-methylphenyl)-chlorobenzo-triazole | Compound 1 | 2-(2-Hydroxy-3-t-butyl-5-methylphenyl)-chlorobenzo-triazole | Compound 1 | 2-(2-Hydroxy-3-t-butyl-5-methylphenyl)-chlorobenzo-triazole | Compound 1 | 2-(2-Hydroxy-3-t-butyl-5-methylphenyl)-chlorobenzo-triazole |
| Addition ratio of ultraviolet absorbing agent (%) | 0.49 | 0.75 | 0.53 | 0.85 | 0.53 | 0.75 | 0.27 | 0.50 |
| Refractive index of resin | 1.60 | 1.60 | 1.60 | 1.60 | 1.60 | 1.60 | 1.67 | 1.67 |
| Transmisstance at 410 nm (%) | 0.9 | 1.3 | 1.0 | 1.1 | 1.0 | 1.2 | 0.9 | 1.1 |
| Transmisstance at 415 nm (%) | 5.6 | 8.4 | 4.8 | 6.4 | 6.5 | 8.3 | 4.9 | 6.7 |
| Transmittance at 420 nm (%) | 29.0 | 29.8 | 26.4 | 26.2 | 31.5 | 30.0 | 26.3 | 24.8 |
| Transmittance at 425 nm (%) | 58.7 | 55.8 | 56.7 | 52.8 | 60.8 | 56.1 | 54.4 | 49.7 |
| Transmittance at 430 nm (%) | 77.0 | 73.9 | 75.7 | 71.8 | 77.6 | 73.8 | 72.6 | 68.8 |
| Transmittance at 440 nm (%) | 88.0 | 86.7 | 87.4 | 86.5 | 87.0 | 86.4 | 84.7 | 84.1 |
| Luminous transmittance (%) | 89.8 | 89.4 | 90.2 | 90.0 | 89.4 | 89.4 | 88.3 | 88.2 |
| (Transmittance at 425 nm) − (Transmittance at 420 nm) | 29.7 | 26.0 | 30.3 | 26.6 | 29.2 | 26.1 | 28.0 | 24.9 |
| (Transmittance at 425 nm) − (Transmittance at 415 nm) | 53.1 | 47.4 | 51.9 | 46.4 | 54.2 | 47.8 | 49.4 | 43.0 |

TABLE 3-continued

|  | | | | | | | | |
|---|---|---|---|---|---|---|---|---|
| [(Transmittance at 425 nm) − (Transmittance at 415 nm)] × [(Refractive index of resin) − 0.6] | 53.1 | 47.4 | 51.9 | 46.4 | 54.2 | 47.8 | 52.9 | 46.0 |
| YI | 7.6 | 8.2 | 8.0 | 8.6 | 7.3 | 8.1 | 8.5 | 9.3 |
| Comparison of coloration (yellowness degree) | ○ | X | ○ | X | ○ | X | ○ | X |
| Exucidation of ultraviolet absorbing agent from resin | No Transparent | No Transparent | No Transparent | No Transparent | No Transparent | No Transparent | No Transparent | No Transparent |
| Light resistance ΔYI (2 mm thickness) 100 hr | 0.1 | 0.2 | — | — | 0.4 | 0.4 | — | — |
| Light resistance ΔYI (2 mm thickness) 20 hr | — | — | — | — | — | — | 0.0 | 0.0 |
| Heat resistance ΔYI (5 mm thickness) 60° C. 1 week | 0.0 | 0.2 | — | — | 0.1 | 0.1 | 0.0 | 0.2 |
| Heat resistance ΔYI (5 mm thickness) 150° C. 1 hr | — | — | — | — | 0.1 | 0.2 | — | — |
| Refractive index of resin (546 nm) | — | — | — | — | 1.6038 | 1.6038 | — | — |
| Abbe's number of resin (546 nm) | — | — | — | — | 41.1 | 39.5 | — | — |

|  | Example 5 | Comparative Example 5 | Example 6 | Example 7 | Example 8 | Example 9 | Example 10 |
|---|---|---|---|---|---|---|---|
| Type of ultraviolet absorbing agent | Compound 1 | 2-(2-Hydroxy-3-t-butyl-5-methylphenyl)-chlorobenzo-triazole | Compound 2 | Compound 4 | Compound 6 | Compound 7 | Compound 8 |
| Addition ratio of ultraviolet absorbing agent (%) | 0.23 | 0.30 | 0.56 | 0.58 | 0.43 | 0.47 | 0.53 |
| Refractive index of resin | 1.76 | 1.76 | 1.60 | 1.60 | 1.60 | 1.60 | 1.60 |
| Transmisstance at 410 nm (%) | 0.7 | 0.9 | 0.8 | 1.0 | 0.9 | 0.8 | 0.9 |
| Transmisstance at 415 nm (%) | 2.3 | 5.8 | 6.1 | 7.7 | 6.3 | 5.5 | 5.3 |
| Transmittance at 420 nm (%) | 17.7 | 22.5 | 30.1 | 32.7 | 30.5 | 28.6 | 28.0 |
| Transmittance at 425 nm (%) | 46.9 | 46.2 | 58.8 | 60.3 | 59.0 | 58.1 | 57.6 |
| Transmittance at 430 nm (%) | 67.8 | 64.7 | 76.0 | 76.6 | 76.1 | 76.5 | 75.7 |
| Transmittance at 440 nm (%) | 81.5 | 79.8 | 87.0 | 86.5 | 86.8 | 86.8 | 86.9 |
| Luminous transmittance (%) | 85.9 | 85.8 | 89.5 | 89.4 | 89.8 | 89.6 | 89.6 |
| (Transmittance at 425 nm) − (Transmittance at 420 nm) | 29.2 | 23.7 | 28.7 | 27.6 | 28.5 | 29.5 | 29.6 |
| (Transmittance at 425 nm) − (Transmittance at 415 nm) | 44.6 | 40.4 | 52.7 | 52.6 | 52.7 | 52.6 | 52.3 |
| [(Transmittance at 425 nm) − (Transmittance at 415 nm)] × [(Refractive index of resin) − 0.6] | 51.7 | 46.9 | 52.7 | 52.6 | 52.7 | 52.6 | 52.3 |
| YI | 10.0 | 10.8 | 7.9 | 7.7 | 7.9 | 7.9 | 7.9 |
| Comparison of coloration (yellowness degree) | ○ | X | ○ | ○ | ○ | ○ | ○ |
| Exucidation of ultraviolet absorbing agent from resin | No Transparent | No Transparent | No Transparent | No Transparent | No Transparent | No Transparent | No Transparent |
| Light resistance ΔYI (2 mm thickness) 100 hr | — | — | — | — | — | — | — |

TABLE 3-continued

| | | | | | | | |
|---|---|---|---|---|---|---|---|
| Light resistance ΔYI (2 mm thickness) 20 hr | 13.0 | 13.0 | — | — | — | — | — |
| Heat resistance ΔYI (5 mm thickness) 60° C. 1 week | 0.0 | 0.0 | — | — | — | — | — |
| Heat resistance ΔYI (5 mm thickness) 150° C. 1 hr | — | — | — | — | — | — | — |
| Refractive index of resin (546 nm) | — | — | — | — | — | — | — |
| Abbe's number of resin (546 nm) | — | — | — | — | — | — | — |

Compared to 2-(2-hydroxy-3-t-butyl-5-methylphenyl)-chlorobenzotriazole with the molecular weight of 316, the compounds 1 to 14 have molecular weight of more than 360. Nevertheless, the compounds 1 to 14 were dissolved well in the monomer similar to 2-(2-hydroxy-3-t-butyl-5-methylphenyl)-chlorobenzotrizole and there is no exudation on the obtained plastic lens. As such, it was confirmed that affinity for monomer and plastic lens is exhibited due to the structure of the ultraviolet absorbing agent of the present invention.

Furthermore, compared to a lens using 2-(2-hydroxy-3-t-butyl-5-methylphenyl)-chlorobenzotriazole, the plastic lens using the ultraviolet absorbing agent represented by the formula (I) absorbs more efficiently, even, at little addition amount, light with a wavelength of from 400 to 420 nm and shows good transmittance for light with a wavelength of around 420 nm or longer while suppressing a bad influence on eyes, and thus yellow coloration of a plastic lens was suppressed.

Furthermore, it was possible to obtain a lens with appearance having high Abbe's number and excellent optical performance without lowering refractive index of a resin, and a lens which is excellent in heat resistance and, light resistance was obtained.

With regard to the heat resistance, the thermal decomposition temperature of an ultraviolet absorbing agent (for example, 5 wt % weight loss temperature) is a physical property that is important in resin processing at very high temperature. In the present examples, heat yellowing resistance of a lens was determined in an accelerated manner under constant temperature and constant time conditions in order to confirm the heat resistance of a lens (i.e., resin) added with the ultraviolet absorbing agent under the conditions for use.

The lens added with the compound of the present examples yielded the results that are more excellent overall than the lens added with 2-(2-hydroxy-3-t-butyl-5-methylphenyl)-chlorobenzotriazole, and it was confirmed that excellent heat resistance (i.e., heat yellowing resistance) is shown from the compound of the present example, and also from the resin added with the compound of the present invention.

With regard to the light resistance, because the compound of the present examples and 2-(2-hydroxy-3-t-butyl-5-methylphenyl)-chlorobenzotriazole as the compound of Comparative Examples have a different absorption peak and the lens resin also absorbs light, the light yellowing resistance was determined by irradiating not only the light absorption wavelength of an ultraviolet absorbing agent but also, in accelerated manner, the light having a rather broad wavelength range as based on the use of a lens.

The lens added with the compound of the present examples yielded the results that are more excellent overall than the lens added with 2-(2-hydroxy-3-t-butyl-5-methylphenyl)-chlorobenzotriazole, and it was confirmed that excellent light resistance is shown from the compound of the present example, and also from the resin added with the compound of the present example.

The invention claimed is:

1. A plastic lens comprising an ultraviolet absorbing agent which is represented by the following formula (I):

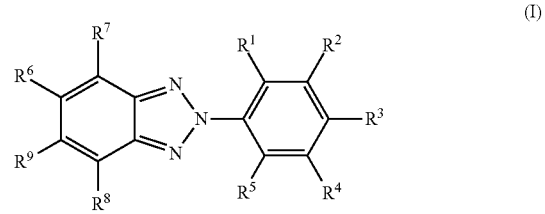

(I)

in the formula, $R^1$ to $R^8$ each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom; $R^9$ represents a monovalent sulfur-containing group which is represented by the following formula (i):

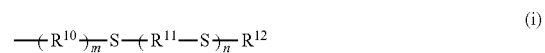

(i)

in the formula, $R^{10}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom, $R^{11}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom when n is 2 or higher, $R^{11}$ represents a hydrogen atom or a group represented by —$(R^{13})_p$—$R^{14}$, wherein $R^{13}$ represents a divalent hydrocarbon group with 1 to 20 carbon atoms which may be substituted a hydrogen atom with, interrupted a proximal terminal by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom, and $R^{14}$ represents a hydrogen atom or a substituent group containing any one skeleton selected from benzotriazole, benzophenone, benzoic acid ester, and triazine; p represents an integer of 0 or 1; total number of carbon atoms in $R^{10}$, n number of $R^{11}$, and $R^{12}$ is 30 or less; m represents an integer of 0 or 1; n represents an integer of 0 to 3; and a resin material.

2. The plastic lens according to claim 1, wherein the monovalent sulfur-containing group represented by the formula (i) is represented by the formula (i-1) in which m is 0:

(i-1)

in the formula, $R^{11}$, and n are as defined in the above.

3. The plastic lens according to claim 2, wherein in the formula (i-1), $R^{11}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom when n is 2 or higher, represents a hydrogen atom or a group represented by —$(R^{13})_p$—H wherein $R^{13}$ represents a divalent hydrocarbon group with 1 to 20 carbon atoms which may be substituted a hydrogen atom with, interrupted a proximal terminal by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom.

4. The plastic lens according to claim 2, wherein in the formula (i-1), $R^{11}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom when n is 2 or higher, $R^{12}$ represents a hydrogen atom or a group represented by —$(R^{13})_p$—H wherein $R^{13}$ represents a divalent hydrocarbon group with 1 to 20 carbon atoms which may be substituted a hydrogen atom with, interrupted a proximal terminal by or interrupted a carbon-carbon bond by a monovalent group or a divalent group selected from an aromatic group, an unsaturated group, a sulfur-containing group, an oxygen-containing group, a phosphorus-containing group, an alicyclic group, and a halogen atom, and wherein the ultraviolet absorbing agent of the formula (I) has a light absorption peak present in 350 to 390 nm in 100 μM chloroform solution, the absorption peak present in the wavelength ranges is a maximum absorption wavelength ($\lambda_{max}$), the gradient at longer wavelength side of the absorption peak, which is an absolute value of gradient of a straight line connected between an absorption peak and a peak end of an absorption spectrum at longer wavelength side, is 0.025 or more, the maximum molar absorption coefficient ($\varepsilon\lambda_{max}$) of the absorption peak is 17000 L/(mol·cm) or more.

5. The plastic lens according to claim 4, wherein $R^{11}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group with carbon atom number of 6 to 18, an unsaturated group with carbon atom number of 1 to 10, a sulfur-containing group with carbon atom number of 0 to 10, an oxygen-containing group with carbon atom number of 6 to 12 when it includes an aromatic ring group or an alicyclic group, or carbon atom number of 0 to 6 when it does not include an aromatic ring group or an alicyclic group, a phosphorus-containing group with carbon atom number of 6 to 22 when it includes an aromatic ring group or an alicyclic group, or carbon atom number of 0 to 6 when it does not include an aromatic ring group or an alicyclic group, and an alicyclic group with carbon atom number of 3 to 10, $R^{12}$ represents a group represented by —$R^{13}$—H, and $R^{13}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group with carbon atom number of 6 to 18, an unsaturated group with carbon atom number of 1 to 10, a sulfur-containing group with carbon atom number of 0 to 10, an oxygen-containing group with carbon atom number of 6 to 12 when it includes an aromatic ring group or an alicyclic group, or carbon atom number of 0 to 6 when it does not include an aromatic ring group or an alicyclic group, a phosphorus-containing group with carbon atom number of 6 to 22 when it includes an aromatic ring group or an alicyclic group, or carbon atom number of 0 to 6 when it does not include an aromatic ring group or an alicyclic group, and an alicyclic group with carbon atom number of 3 to 10.

6. The plastic lens according to claim 5, wherein the hydrocarbon group of $R^{11}$ and $R^{13}$ is a linear or branched alkylene group which may be interrupted at least any one of two terminals by an aromatic group or an alicyclic group and the carbon-carbon bond is not interrupted, the hydrogen atom is not substituted by the monovalent group or the divalent group, or substituted with the monovalent group or the divalent group with number of 2 or less, and the monovalent group or the divalent group is a hydroxy group or a vinyl group.

7. The plastic lens according to claim 3, wherein the hydrocarbon group of $R^{11}$ and $R^{13}$ is a linear alkylene group in which the two terminals and the carbon-carbon bond is not interrupted and the hydrogen atom is not substituted.

8. The plastic lens according to claim 4, wherein the gradient at longer wavelength side of the absorption peak which is a maximum absorption wavelength ($\lambda_{max}$) in 100 μM chloroform solution of the ultraviolet absorbing agent represented by the formula (I) is 0.030 or more.

9. The plastic lens according to claim 8, wherein the gradient at longer wavelength side of the absorption peak of the ultraviolet absorbing agent represented by the formula (I) is 0.030 or more, the maximum molar absorption coefficient ($\varepsilon\lambda_{max}$) of the absorption peak is 18000 L/(mol·cm) or more.

10. The plastic lens according to claim 8, wherein the molecular weight of the ultraviolet absorbing agent represented by the formula (I) is 550 or less.

11. The plastic lens according to claim 2, wherein the light transmittance measured at a thickness of 2 mm satisfies at least one of the following characteristics [a] to [c]:
[a] (transmittance % at 425 nm)−(transmittance % at 415 nm) is 50% or higher, or transmittance at 415 nm is 5% or lower;
[b] (transmittance % at 425 nm)−(transmittance % at 420 nm) is 27% or higher; and
[c] [(transmittance % at 425 nm)−(transmittance % at 415 nm)]×(refractive index of resin−0.6) is 50% or higher.

12. The plastic lens according to claim 2, wherein $R^9$ of the formula (I) is the monovalent sulfur-containing group which is represented by the following formula (i):

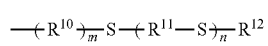
(i)

in the formula, $R^{12}$ represents a group represented by —$(R^{13})_p$—$R^{14}$,
$R^{10}$, $R^{11}$ and $R^{13}$ represents a divalent hydrocarbon group with 1 to 20 carbon atoms which may be substituted a hydrogen atom with, interrupted at least any one of two terminals by or interrupted a carbon-carbon bond by a monovalent group or a divalent group selected from an aromatic group with carbon atom number of 6 to 18, an unsaturated group with carbon atom number of 1 to 10, a sulfur-containing group with carbon atom number of 0 to 10, an oxygen-containing group with carbon atom number of 6 to 12 when it includes an aromatic ring group or an alicyclic group, or carbon atom number of 0 to 6 when it does not include an aromatic ring group or an alicyclic group, a phosphorus-containing group with carbon atom number of 6 to 22 when it includes an aromatic ring group or an alicyclic group, or carbon atom number of 0 to 6 when it does not include an aromatic ring group or an alicyclic group, and an alicyclic group with carbon atom number of 3 to 10,
$R^{14}$ represents a substituent group containing any one skeleton selected from benzotriazole, benzophenone, benzoic acid ester, and triazine,
the substituent group containing benzotriazole is represented by the following formula (A):

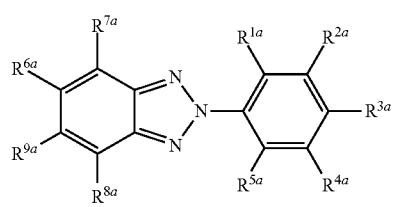
(A)

in the formula (A), any one of $R^{1a}$ to $R^{9a}$ represents a monovalent binding part which binds to $R^{13}$ of the formula (i) or the terminal sulfur atom, and $R^{1a}$ to $R^{9a}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom, the substituent group containing benzophenone is represented by the following formula (B):

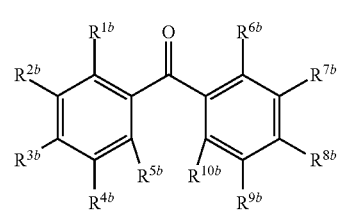
(B)

in the formula (B), any one of $R^{1b}$ to $R^{10b}$ represents a monovalent binding part which binds to $R^{13}$ of the formula (i) or the terminal sulfur atom, and $R^{1b}$ to $R^{10b}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom, the substituent group containing benzoic acid ester is represented by the following formula (C):

[Chemical Formula 7]

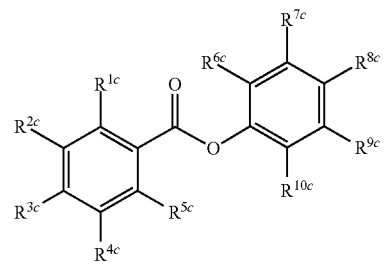
(C)

in the formula (C), any one of $R^{1c}$ to $R^{10c}$ represents a monovalent binding part which binds to $R^{13}$ of the formula (i) or the terminal sulfur atom, and $R^{1c}$ to $R^{10c}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom, the substituent group containing triazine is represented by the following formula (D):

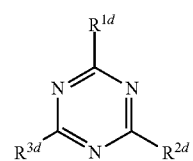
(D)

in the formula (D), $R^{1d}$ to $R^{3d}$ represents any one of the following [A] and [B]:
[A] At least one of $R^{1d}$ to $R^{3d}$ represents a monovalent binding part which binds to $R^{13}$ of the formula (i) or the terminal sulfur atom, and $R^{1d}$ to $R^{3d}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, a halogen atom, and a group represented by the following formula (d):

[Chemical Formula 9]

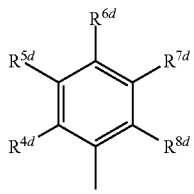
(d)

in the formula, $R^{od}$ to $R^{8d}$ each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom;

[B] at least one of $R^{id}$ to $R^{ad}$ represents a group represented by the following formula (d'):

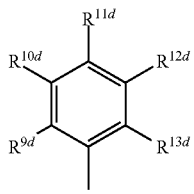
(d')

at least one of $R^{9d}$ to $R^{13d}$ represents a monovalent binding part which binds to $R^{13}$ of the formula (i) or the terminal sulfur atom, and $R^{9d}$ to $R^{13d}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom, and $R^{1d}$ to $R^{3d}$ other than that each independently represent a monovalent group selected from a hydrogen atom, a hydrocarbon group with 1 to 10 carbon atoms, an aromatic group, an unsaturated group, a sulfur-containing group, an oxygen-containing group, a phosphorus-containing group, an alicyclic group, and a halogen atom, in the substituent group containing any one skeleton selected from benzotriazole, benzophenone, benzoic acid ester, and triazine of $R^{14}$, the aromatic group has carbon atom number of 6 to 18, the unsaturated group has carbon atom number of 1 to 10, the sulfur-containing group has carbon atom number of 0 to 10, the oxygen-containing group has carbon atom number of 6 to 12 when it includes an aromatic ring group or an alicyclic group, or carbon atom number of 0 to 6 when it does not include an aromatic ring group or an alicyclic group, the phosphorus-containing group has carbon atom number of 6 to 22 when it includes an aromatic ring group or an alicyclic group, or carbon atom number of 0 to 6 when it does not include an aromatic ring group or an alicyclic group, and the alicyclic group has carbon atom number of 3 to 10, total number of carbon atoms in $R^{10}$, n number of $R^{11}$, and $R^{12}$ is 30 or less, m represents an integer of 0 or 1, n represents an integer of 0 to 3.

13. The plastic lens according to claim 12, wherein the monovalent sulfur-containing group represented by the formula (i) is represented by the formula (i-1) in which m is 0:

(i-1)

in the formula, $R^{11}$, $R^{12}$ and n are as defined in the above, $R^{11}$ and $R^{13}$ is a linear alkylene group which is not substituted by the monovalent group or the divalent group, or substituted with the monovalent group or the divalent group with number of 2 or less, and $R^{14}$ represents the substituent group (A) containing benzotriazole skeleton.

14. The plastic lens claim 1, wherein the resin material is a thermosetting resin.

15. The plastic lens claim 2, wherein the resin material is a thermosetting resin.

16. The plastic lens according to claim 1, wherein at least one resin selected from the group consisting of an episulfide resin and a thiourethane resin is contained as the resin material.

17. The plastic lens according to claim 2, wherein at least one resin selected from the group consisting of an episulfide resin and a thiourethane resin is contained as the resin material.

18. The plastic lens claim 1, wherein the resin material is a thermoplastic resin.

19. The plastic lens claim 2, wherein the resin material is a thermoplastic resin.

* * * * *